(12) United States Patent
Tulley et al.

(10) Patent No.: US 7,848,788 B2
(45) Date of Patent: Dec. 7, 2010

(54) MAGNETIC RESONANCE IMAGING PROBE

(75) Inventors: Steve Tulley, Columbia, MD (US);
Albert C. Lardo, Baldwin, MD (US);
Parag Karmarkar, Elliott City, MD (US); Elliot McVeigh, Phoenix, MD (US); Henry R. Halperin, Baltimore, MD (US); Christine Enger McNamara, Chelmsford, MA (US); Paul A. Bottomley, Columbia, MD (US); Ergin Atalar, Columbia, MD (US); Xiaoming Yang, Baltimore, MD (US)

(73) Assignees: The Johns Hopkins University, Baltimore, MD (US); SurgiVision, Inc., Marietta, GA (US)

( * ) Notice: Subject to any disclaimer, the term of this patent is extended or adjusted under 35 U.S.C. 154(b) by 2209 days.

(21) Appl. No.: 10/123,065

(22) Filed: Apr. 11, 2002

(65) Prior Publication Data

US 2003/0028095 A1 Feb. 6, 2003

Related U.S. Application Data

(63) Continuation-in-part of application No. 09/536,090, filed on Mar. 24, 2000, now Pat. No. 6,675,033.

(60) Provisional application No. 60/129,364, filed on Apr. 15, 1999, provisional application No. 60/282,993, filed on Apr. 11, 2001.

(51) Int. Cl.
*A61B 5/055* (2006.01)

(52) U.S. Cl. .................. 600/423; 324/318; 324/322

(58) Field of Classification Search .......... 600/410, 600/421–423; 324/307, 309, 318, 322
See application file for complete search history.

(56) References Cited

U.S. PATENT DOCUMENTS

| 3,342,175 | A | 9/1967 | Bulloch | |
|---|---|---|---|---|
| 4,431,005 | A | 2/1984 | McCormick | 128/656 |
| 4,445,501 | A | 5/1984 | Bresler | 128/1.5 |
| 4,554,929 | A | 11/1985 | Samson et al. | 128/772 |
| 4,572,198 | A | 2/1986 | Codrington | 128/653 |
| 4,643,186 | A | 2/1987 | Rosen et al. | 128/303.1 |
| 4,672,972 | A | 6/1987 | Berke | 128/653 |
| 4,682,125 | A | 7/1987 | Harrison et al. | 333/12 |
| 4,766,381 | A | 8/1988 | Conturo et al. | 324/309 |
| 4,776,341 | A | 10/1988 | Bachus et al. | 128/653 |

(Continued)

FOREIGN PATENT DOCUMENTS

EP 0 466 424 A1 1/1992

(Continued)

OTHER PUBLICATIONS

Supplementary European Search Report for 00926003.5-1265/1171032; corresponding to PCT/US0010070, Mailing date Sep. 30, 2008.

(Continued)

*Primary Examiner*—Ruth S Smith
(74) *Attorney, Agent, or Firm*—Frommer Lawrence & Haug LLP; Bruce E. Black

(57) ABSTRACT

Herein is disclosed a magnetic resonance imaging probe, having a probe shaft including a magnetic resonance antenna, and a spring tip attached to a distal end of the antenna.

26 Claims, 22 Drawing Sheets

U.S. PATENT DOCUMENTS

| | | | |
|---|---|---|---|
| 4,791,372 A | 12/1988 | Kirk et al. | 324/318 |
| 4,793,356 A | 12/1988 | Misic et al. | 128/653 |
| 4,808,164 A * | 2/1989 | Hess | 604/95.01 |
| 4,813,429 A | 3/1989 | Eshel et al. | 128/736 |
| 4,823,812 A | 4/1989 | Eshel et al. | 128/804 |
| 4,858,613 A | 8/1989 | Fry et al. | 128/660.03 |
| 4,859,950 A | 8/1989 | Keren | 324/322 |
| 4,897,604 A | 1/1990 | Carlson et al. | 324/318 |
| 4,922,204 A | 5/1990 | Duerr et al. | 324/322 |
| 4,932,411 A | 6/1990 | Fritschy et al. | 128/653 |
| 4,960,106 A | 10/1990 | Kubokawa | 128/6 |
| 5,019,075 A | 5/1991 | Spears et al. | 606/7 |
| 5,035,231 A | 7/1991 | Kubokawa et al. | 128/6 |
| 5,050,607 A | 9/1991 | Bradley et al. | 128/653 A |
| 5,090,959 A | 2/1992 | Samson et al. | 604/96 |
| 5,095,911 A | 3/1992 | Pomeranz | 128/662.06 |
| 5,099,208 A | 3/1992 | Fitzpatrick et al. | 324/312 |
| 5,167,233 A | 12/1992 | Eberle et al. | 128/662.06 |
| 5,170,789 A | 12/1992 | Narayan et al. | 128/653.5 |
| 5,190,046 A | 3/1993 | Shturman | 128/662.06 |
| 5,211,165 A | 5/1993 | Dumoulin et al. | 128/653.1 |
| 5,211,166 A | 5/1993 | Sepponen | |
| 5,217,010 A | 6/1993 | Tsitlik et al. | 128/419 PG |
| 5,260,658 A | 11/1993 | Greim et al. | 324/322 |
| 5,270,485 A | 12/1993 | Jacobsen | 174/15.1 |
| 5,271,400 A | 12/1993 | Dumoulin et al. | 128/653.2 |
| 5,293,872 A | 3/1994 | Alfano et al. | 128/664 |
| 5,294,886 A | 3/1994 | Duerr | 324/318 |
| 5,307,808 A | 5/1994 | Dumoulin et al. | 128/653.2 |
| 5,307,814 A | 5/1994 | Kressel et al. | 128/653.5 |
| 5,318,025 A | 6/1994 | Dumoulin et al. | 128/653.2 |
| 5,323,778 A | 6/1994 | Kandarpa et al. | 128/653.2 |
| 5,347,221 A | 9/1994 | Rubinson | 324/318 |
| 5,348,010 A | 9/1994 | Schnall et al. | 128/653.2 |
| 5,352,979 A | 10/1994 | Conturo | 324/307 |
| 5,355,087 A | 10/1994 | Claiborne et al. | 324/322 |
| 5,358,515 A | 10/1994 | Hürter et al. | 607/101 |
| 5,365,928 A | 11/1994 | Rhinehart et al. | 128/653.5 |
| 5,370,644 A | 12/1994 | Langberg | 606/33 |
| 5,372,138 A | 12/1994 | Crowley et al. | 128/662.06 |
| 5,375,596 A | 12/1994 | Twiss et al. | 128/653.1 |
| 5,383,467 A * | 1/1995 | Auer et al. | 600/342 |
| 5,400,787 A | 3/1995 | Marandos | 128/653.5 |
| 5,411,476 A | 5/1995 | Abrams et al. | 604/95 |
| 5,413,104 A | 5/1995 | Buijs et al. | 128/653.5 |
| 5,419,325 A | 5/1995 | Dumoulin et al. | 128/653.2 |
| 5,421,338 A | 6/1995 | Crowley et al. | 128/662.06 |
| 5,429,132 A | 7/1995 | Guy et al. | 128/653.1 |
| 5,435,302 A | 7/1995 | Lenkinski et al. | 600/422 |
| 5,437,277 A | 8/1995 | Dumoulin et al. | 128/653.1 |
| 5,439,000 A | 8/1995 | Gunderson et al. | 128/664 |
| 5,443,066 A | 8/1995 | Dumoulin et al. | 128/653.1 |
| 5,443,489 A | 8/1995 | Ben-Haim | 607/115 |
| 5,447,156 A | 9/1995 | Dumoulin et al. | 128/653.2 |
| 5,451,232 A | 9/1995 | Rhinehart et al. | 606/192 |
| 5,451,774 A | 9/1995 | Jacobsen | 250/227.24 |
| 5,462,055 A | 10/1995 | Casey et al. | 128/653.5 |
| 5,476,095 A | 12/1995 | Schnall et al. | 128/653.2 |
| 5,498,261 A | 3/1996 | Strul | 606/29 |
| 5,507,743 A | 4/1996 | Edwards et al. | 606/41 |
| 5,512,825 A | 4/1996 | Atalar et al. | 324/309 |
| 5,520,644 A | 5/1996 | Imran | 604/95 |
| 5,524,630 A | 6/1996 | Crowley | 128/662.06 |
| 5,540,679 A | 7/1996 | Fram et al. | 606/27 |
| 5,558,093 A | 9/1996 | Pomeranz | 128/660.03 |
| 5,572,132 A | 11/1996 | Pulyer et al. | |
| 5,578,008 A | 11/1996 | Hara | 604/96 |
| 5,588,432 A | 12/1996 | Crowley | 128/660.03 |
| 5,598,097 A | 1/1997 | Scholes et al. | 324/316 |
| 5,609,606 A | 3/1997 | O'Boyle | 606/194 |
| 5,611,807 A | 3/1997 | O'Boyle | 606/169 |
| 5,623,241 A | 4/1997 | Minkoff | 335/296 |
| 5,647,361 A | 7/1997 | Damadian | 128/683.2 |
| 5,660,180 A | 8/1997 | Malinowski et al. | 128/660.03 |
| 5,682,897 A | 11/1997 | Pomeranz | 128/662.06 |
| 5,699,801 A | 12/1997 | Atalar et al. | 128/653.2 |
| 5,715,825 A | 2/1998 | Crowley | 128/602.06 |
| 5,728,079 A | 3/1998 | Weber et al. | 604/280 |
| 5,738,632 A | 4/1998 | Karasawa | 600/410 |
| 5,775,338 A | 7/1998 | Hastings | 128/898 |
| 5,792,055 A | 8/1998 | McKinnon | 600/410 |
| 5,833,608 A | 11/1998 | Acker | 600/409 |
| 5,833,632 A | 11/1998 | Jacobsen et al. | 600/585 |
| 5,840,031 A | 11/1998 | Crowley | 600/440 |
| 5,868,674 A | 2/1999 | Glowinski et al. | 600/410 |
| 5,916,162 A | 6/1999 | Snelten et al. | 600/411 |
| 5,928,145 A | 7/1999 | Ocali | |
| 5,938,609 A | 8/1999 | Pomeranz | 600/439 |
| 5,938,692 A | 8/1999 | Rudie | 607/101 |
| 5,964,705 A | 10/1999 | Truwit et al. | 600/423 |
| 5,968,052 A | 10/1999 | Sullivan, III et al. | 606/108 |
| 6,004,269 A | 12/1999 | Crowley et al. | 600/439 |
| 6,011,995 A | 1/2000 | Guglielmi et al. | 607/99 |
| 6,019,737 A | 2/2000 | Murata | 600/585 |
| 6,026,316 A | 2/2000 | Kucharczyk et al. | 600/420 |
| 6,031,375 A | 2/2000 | Atalar et al. | 324/307 |
| 6,032,078 A | 2/2000 | Rudie | 607/101 |
| 6,051,974 A | 4/2000 | Reisker et al. | 324/318 |
| 6,058,323 A | 5/2000 | Lemelson | 600/408 |
| 6,061,587 A | 5/2000 | Kurcharczyk et al. | 600/411 |
| 6,064,203 A | 5/2000 | Bottomley | 324/309 |
| 6,078,831 A | 6/2000 | Belef et al. | 600/424 |
| 6,104,943 A | 8/2000 | Frederick et al. | 600/410 |
| 6,171,240 B1 | 1/2001 | Young et al. | 600/410 |
| 6,171,241 B1 | 1/2001 | McVeigh et al. | 600/410 |
| 6,188,219 B1 | 2/2001 | Reeder et al. | 324/307 |
| 6,233,474 B1 | 5/2001 | Lemelson | 600/411 |
| 6,263,229 B1 | 7/2001 | Atalar et al. | 600/423 |
| 6,272,370 B1 | 8/2001 | Gillies et al. | 600/411 |
| 6,284,971 B1 | 9/2001 | Atalar et al. | 174/36 |
| 6,332,089 B1 | 12/2001 | Acker et al. | 600/424 |
| 6,351,124 B1 | 2/2002 | Vester et al. | 324/318 |
| 6,408,202 B1 | 6/2002 | Lima et al. | 600/423 |
| 6,549,800 B1 | 4/2003 | Atalar et al. | 600/423 |
| 6,628,980 B2 * | 9/2003 | Atalar et al. | 600/423 |
| 6,675,033 B1 * | 1/2004 | Lardo et al. | 600/410 |
| 6,714,809 B2 * | 3/2004 | Lee et al. | 600/423 |
| RE40,587 E * | 11/2008 | McKinnon | 600/410 |
| 2001/0056232 A1 | 12/2001 | Lardo et al. | 600/423 |
| 2002/0040185 A1 | 4/2002 | Atalar et al. | 600/423 |
| 2002/0045816 A1 | 4/2002 | Atalar et al. | 600/423 |
| 2002/0097050 A1 | 7/2002 | Kellman et al. | 324/309 |
| 2002/0161421 A1 | 10/2002 | Lee et al. | 607/116 |
| 2002/0177771 A1 | 11/2002 | Guttman et al. | 600/410 |
| 2003/0028094 A1 | 2/2003 | Kumar et al. | 600/410 |
| 2003/0028095 A1 | 2/2003 | Tulley et al. | 600/422 |
| 2003/0050557 A1 | 3/2003 | Susil et al. | 600/424 |
| 2004/0220470 A1 * | 11/2004 | Karmarkar et al. | 600/423 |

FOREIGN PATENT DOCUMENTS

| | | |
|---|---|---|
| EP | 0 557 127 A2 | 8/1993 |
| EP | 0 659 385 A1 | 6/1995 |
| EP | 0 557 127 A3 | 3/1996 |
| EP | 0 768 539 A2 | 4/1997 |
| EP | 0 850 595 A1 | 7/1998 |
| EP | 0 908 739 A2 | 4/1999 |
| JP | 6-70902 | 3/1994 |
| JP | 09103415 | 4/1994 |
| WO | 9822030 | 5/1998 |
| WO | WO 98/52064 | 11/1998 |
| WO | WO 98/52461 | 11/1998 |
| WO | WO 99/18852 | 4/1999 |
| WO | WO 99/27390 | 6/1999 |

| WO | WO 99/59479 | 11/1999 |
| WO | WO 00/64003 | 10/2000 |
| WO | WO 00/64003 A | 10/2000 |

OTHER PUBLICATIONS

Gilderdale, D.J., A Dedicated Internal Coil for Imaging the Female Urethra, I.R. Proceedings of the Society of Magnetic Resonance in Medicine. Meeting 4, p. 1437, Apr. 27, 1996.

Desouza, N. M., Magnetic Resonance Imaging of the Anal Sphincter Using an Internal Coil, Magnetic Resonance Quarterly, vol. 11 No. 1, pp. 45-56, 1995.

EPO Communication for European Patent Application Serial No. 00926003.5 mailed Jul. 1, 2009.

Lardo, A.C.; "Real-Time Magnetic Resonance Imaging: Diagnostic and Interventional Applications", Pediatric Cardiology, Springer-Verlag, NY, US., vol. 21, No. 1: 80-98, (Jan. 2000).

Form PCT/ISA/210, International Search Report for PCT/US 01/03346 (Nov. 5, 2001), Applicant: Surgi-Vision, Inc.

Ladd et al.; "Guidewire Antennas for MR Fluoroscopy", Magnetic Resonance in Medicine, Academic Press, Duluth, MN, US., vol. 37(6): 891-897, (Jun. 1, 1997).

Martin et al.; "An Expandable Intravenous RF Coil For Imaging the Artery Wall", Proceeding of the International Society for Magnetic Resonance In Medicine, Fourth Scientific Meeting and Exhibition, New York, USA Apr. 27-May 3, 1996, vol. 1, p. 402.

Quick et al; "Vascular Stents as RF-Antennas for Intravascular MR-Guidance and- Imaging", Proceedings of the International Society for Magnetic Resonance in Medicine, Seventh Scientific Meeting and Exhibition, Philadelphia, Pennsylvania, USA May 22-28, 1999, vol. 1, p. 577.

Atalar et al.;"High Resolution Intravascular MRI and MRS using a Catheter Receiver Coil,", Magnetic Resonance in Medicine, 36:596-605 (1996).

Edelman et al.; "Magnetic Resonance Imaging" NEJM 328: 708-716 (1993).

Farmer et al., "Implanted Coil MR Microscopy of RenalPathology", Magn. Reson. Med., 10: 310-323 (1989).

Garwood et al.;"Magnetic Resonance Imaging with Adiabatic Using a Single Surface Coil for RF Transmission and Signal Detection", Magnetic Resonance in Medicine 9: 25-34 (1989).

Hoult et al.; "The Signal-to-Noise Ratio of the Nuclear Magnetic Resonance Experiment" J. Magn. Reson., 24: 71-85 (1976).

Hoult; "Rotating Frame Zeugmatography", Phil. Trans. R. Soc. Lond. B. 289: 543-547 (1980).

Jolesz et al. ; "Interventional Magnetic Resonance Therapy", Seminars in Interventional Radiology ,12: 20-27 (1995).

Ocali et al.; "Intravascular Magnetic Resonance Imaging Using a Loopless Catheter Antenna", MRM, 37: 112-118 (1997).

Silverman et al.; "Interactive MR-guided Biopsy in an Open configuration MR Imaging System", Radiology, 197: 175-181 (1995).

* cited by examiner

AXIAL MODE
D > γ

NORMAL MODE
D << γ

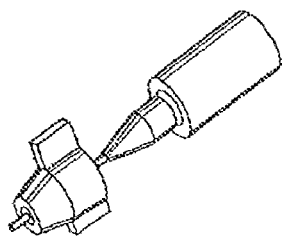
Fig. 24A
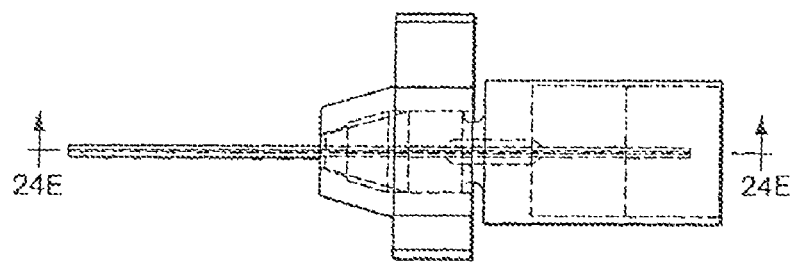
Fig. 24B
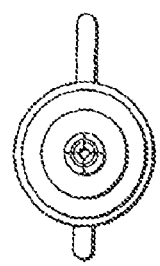 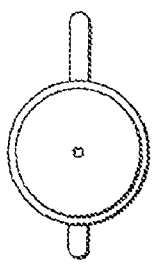
Fig. 24C  Fig. 24D
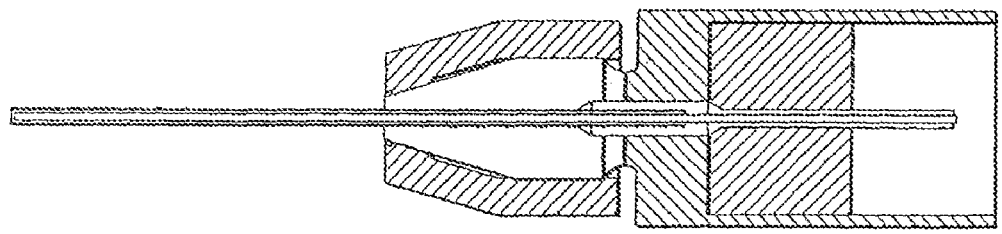
Fig. 24E

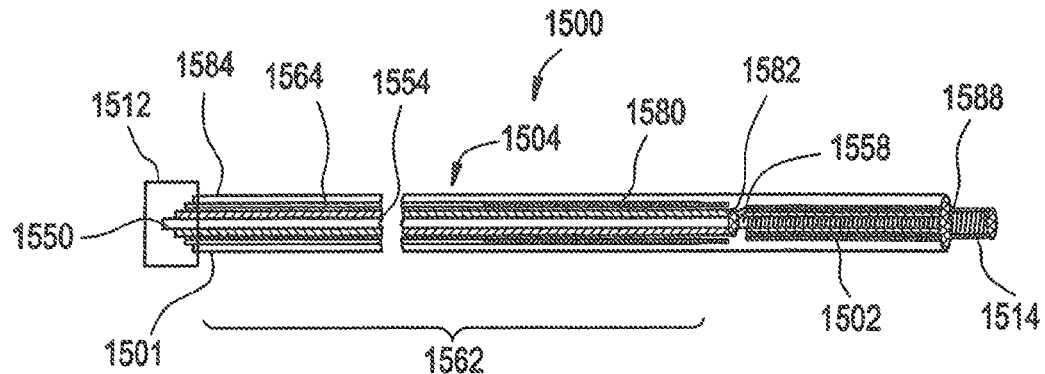
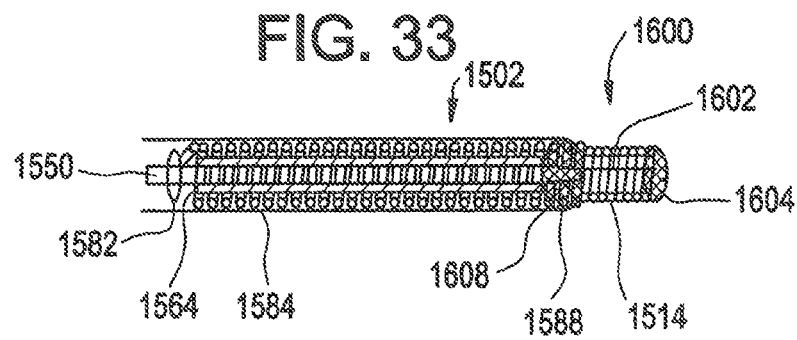
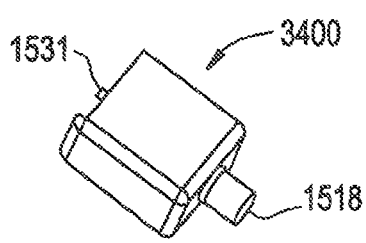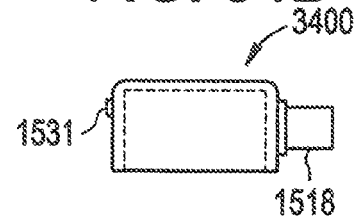
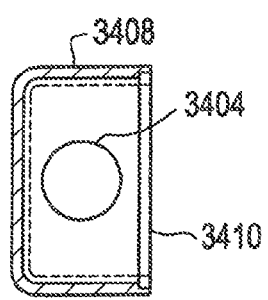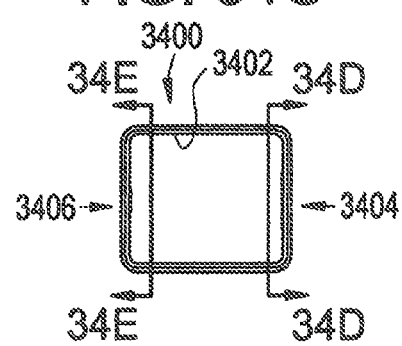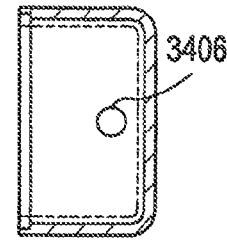

MAGNETIC RESONANCE IMAGING PROBE

CROSS-REFERENCE TO RELATED APPLICATIONS

This application is a continuation-in-part of U.S. patent application Ser. No. 09/536,090, filed Mar. 24, 2000, which issued as U.S. Pat. No. 6,675,033 on Jan. 6, 2004, which claims the benefit of priority to U.S. Provisional Patent Application Ser. No. 60/129,364, filed Apr. 15, 1999. This application also claims benefit of priority to U.S. Provisional Patent Application Ser. No. 60/282,993, filed Apr. 11, 2001. The aforementioned applications are incorporated herein in their entireties by this reference.

BACKGROUND

The disclosed systems, devices, assemblies, probes, and methods relate to the field of radio frequency antennas, more particularly to the use of radio frequency antennas as imaging coils used in vivo in conjunction with magnetic resonance imaging techniques.

Magnetic resonance imaging (MRI) is a well known, highly useful technique for imaging matter. It has particular use with imaging the human body or other biological tissue without invasive procedures or exposure to the harmful radiation or chemicals present with x-rays or CT scans. MRI uses changes in the angular momentum or "spin" of atomic nuclei of certain elements to show locations of those elements within matter. In an MRI procedure, a subject is usually inserted into an imaging machine that contains a large static magnetic field generally on the order of 0.2 to 4 Tesla although machines with higher strength fields are being developed and used. This static magnetic field tends to cause the vector of the magnetization of the atomic nuclei placed therein to align with the magnetic field. The subject is then exposed to pulses of radio frequency (RF) energy in the form of a second, oscillating, RF magnetic field having a particular frequency referred to in the art as a resonant or Larmor frequency. This frequency is equal to the rate that the spins rotate or precess.

This second field is generally oriented so that its magnetic field is oriented in the transverse plane to that of the static magnetic field and is generally significantly smaller. The second field pulls the net magnetism of the atomic nuclei off the axis of the original magnetic field. As the second magnetic field pulses, it pulls the spins off axis. When it is turned off, the spins "relax" back to their position relative to the initial magnetic field. The rate at which the spins relax is dependent on the molecular level environment. During the relaxation step, the precessing magnetization at the Larmor frequency induces a signal voltage that can be detected by antennas tuned to that frequency. The magnetic resonance signal persists for the time it takes for the spin to relax. Since different tissues have different molecular level environments, the differences in relaxation times provides a mechanism for tissue contrast in MRI.

In order to image the magnetic resonance signal it is necessary to encode the locations of the resonant spins. This is performed by applying pulse of gradient magnetic fields to the main magnetic field in each of the three dimensions. By creating this field, the location of resonant nuclei can be determined because the nuclei will resonate at a different Larmor frequency since the magnetic field they experience differs from their neighbors. The magnetic resonance (MR) image is a representation of the magnetic resonance signal on a display in two or three dimensions. This display usually has slices taken on an axis of interest in the subject, or slices in any dimension or combination of dimensions, three-dimensional renderings including computer generated three-dimensional "blow-ups" of two-dimensional slices, or any combination of the previous, but can include any display known to the art.

MR signals are very weak and therefore the antenna's ability to detect them depends on both its size and its proximity to the source of those frequencies. In order to improve the signal of an MRI, the antenna may be placed near or inside the subject to be imaged. Such improvements can enable valuable increases in resolution sensitivity and scan time. It may be desirable to have evidence of the MRI antenna itself on the MRI to allow the individual inserting the MRI antenna to direct where it is going and to maneuver it with aid from the MR image. Such a benefit could be useful in medical procedures where MRI is used simultaneously to track the position of an intraluminal device and to evaluate the structures surrounding the lumen. For example, an intravascular catheter could be directed through a vessel using MRI to reach a targeted area of the vessel, and the MRI apparatus could further be used to delineate the intravascular anatomy or nearby tissue to determine whether a particular therapeutic intervention would be required. Using MRI to guide the catheter and using MRI further to map out the relevant anatomy could complement conventional angiographic imaging technology within an interventional radiology or cardiology or minimally invasive imaging suite. Once the catheter is directed to the desired anatomic target under MR guidance, and once the topography or other relevant anatomy of the target lesion is depicted using MRI, the clinician can make decisions about what type of intervention would be indicated, if any, and where the intervention should be delivered.

Many conventional vascular interventional procedures use X-ray imaging technology in which guidewires and catheters are inserted into a vein or artery and navigated to specific locations in the heart for diagnostic and therapeutic procedures. Conventional X-ray guided vascular interventions, however, suffer from a number of limitations, including: (1) limited anatomical visualization of the body and blood vessels during the examination, (2) limited ability to obtain a cross-sectional view of the target vessel, (3) inability to characterize important pathologic features of atherosclerotic plaques, (4) limited ability to obtain functional information on the state of the related organ, and (5) exposure of the subject to potentially damaging x-ray radiation. MRI techniques offer the potential to overcome these deficiencies.

However, even those antennae which have been fabricated for use inside a human body are not useful for many types of interventional procedures. Many of these devices are simply too large to be sufficiently miniaturized to allow the placement of an interventional device simultaneously with the antenna in a small vessel without causing injury to the subject. Furthermore, many of these devices are not useful as guidewires because the antenna cannot accept the range of interventional tools that are widely used in many types of procedures without removal of the guidewire from the subject during tool transition. This includes, but is not limited to, such tools as balloon catheters for dilatation angioplasties, for stent placements, for drug infusions, and for local vessel therapies such as gene therapies; atherotomes and other devices for plaque resection and debulking; stent placement catheters; intraluminal resecting tools; electrophysiologic mapping instruments; lasers and radio frequency and other ablative instruments.

It is desirable, therefore, to provide an imaging probe suitable for use as a guidewire for intravascular diagnostic and therapeutic maneuvers using MRI techniques. It is further desirable to provide an imaging probe adapted for imaging a vascular structure such as an artery or vein using MRI techniques, such imaging being performed in conjunction with or independent of the introduction of other interventional tools. Providing MRI images of the vascular structure can offer guidance for further diagnostic or therapeutic procedures to be performed.

During the guiding of an imaging probe through tortuous vessels or tortuous peripheral guiding catheters, it is desirable that the distal most portion of the imaging probe steer and track easily. At the same time, interventional angiographers and cardiologists find it advantageous that the probe being manipulated remains intact despite aggressive maneuvering and transmits torque well. An imaging probe with these characteristics may be especially useful in dealing with stenotic or other abnormal vessels, such as may be encountered during various diagnostic and therapeutic interventions. There remains a need in the art for an apparatus that combines the aforesaid handling characteristics with the visualization provided by an endovascular MRI imaging system.

SUMMARY

It is therefore desired in the art to produce a probe that has an antenna suitable to receive and enhance MR images, that antenna providing signal that renders it visible on an MR image and suitable for use as an imaging probe or guidewire.

It is further desired by the art to provide an MRI probe which is constructed of flexible material that has sufficient mechanical properties to be suitable as a directable probe and suitable electrical properties to be an antenna for MRI images rendering it visible on an MR image.

It is further desired by the art to provide an MRI probe which uses multiple different shaped whip antenna designs to allow specific uses under certain circumstances, and which can be used in a clinical environment.

It is further desired by the art to provide an MRI probe that can act as a guidewire to multiple different interventional tools without having to remove the probe from the body to change between tools.

As disclosed herein, one embodiment has a system, method, and means for providing a flexible MRI probe assembly which is capable of receiving magnetic resonance signals from a subject and for functioning as a imaging probe. In one embodiment the MRI probe is small enough to insert into the guidewire lumen of an interventional device as is known to the art.

In a further embodiment, the MRI probe is constructed using materials and designs that optimize mechanical properties for steerability, torque transmission and avoidance of antenna whip failure while maintaining desirable electromagnetic properties in magnetic susceptibly and electrical conductivity.

In yet another embodiment, the MRI probe's antenna whip is constructed to be flexible and therefore reduce the risk of chamber or vessel perforation.

Another embodiment provides a system, method, or means, whereby a guidewire probe suitable for use in an MRI machine can have multiple interventional tools switched between and guided by the guidewire probe without having to remove the probe from the subject. This is accomplished in one embodiment by the design and construction of a probe with a practical connection interface between the probe, the tuning/matching circuitry for tuning the antenna whip, and the MRI machine.

In a further embodiment, the disclosed systems, devices, assemblies, probes, and methods provide a magnetic resonance antenna assembly for receiving magnetic resonance signals from a sample and for functioning as an imaging coil, having a probe shaft including a core of non-magnetic material, a first insulator/dielectric layer for providing insulation, a shielding layer, a second insulator/dielectric layer, and an antenna whip. The core of non-magnetic material may be made of a super-elastic material or shape memory alloy, such as Nitinol. The non-magnetic core may include a coating of conductive material which could have gold, silver, alternating layers of gold and silver or copper, for example. A clip-on connector may be further provided for making an electrical connection to a magnetic resonance scanner, the clip-on connector enabling loading and unloading of interventional devices during a procedure without removal of the probe from the subject. The antenna whip may additionally have a linear whip, a helical whip, a tapered or a combination whip depending on the desired mechanical and electric properties of the antenna whip.

In an embodiment, a magnetic resonance imaging probe can have a probe shaft having a distal end a magnetic resonance antenna having a distal end and attached to the distal end of the probe shaft; and a flexible tip attached to the distal end of the antenna.

In an embodiment, a magnetic resonance imaging probe can include a probe shaft having a magnetic resonance antenna, and a spring tip attached to a distal end of the antenna.

In an embodiment, a magnetic resonance imaging probe can have a probe shaft having a distal end and a proximal end, the probe shaft further having a core of non-magnetic material a first insulator/dielectric, a shield layer having a distal end, and a proximal spring assembly coupled to the distal end of the shield layer, and an imaging coil attached to the distal end of the probe shaft, wherein at least one of the imaging coil and the spring tip may be visible on a magnetic resonance image.

In an embodiment, a magnetic resonance imaging probe can have a probe shaft having a distal end and a proximal end, the probe shaft further having a core of non-magnetic material, a first insulator/dielectric covering the core, and a shield layer covering the core; a magnetic resonance imaging coil attached to the distal end of the probe shaft and having a distal end, and a spring tip attached to the distal end of the imaging coil, wherein at least one of the imaging coil and the spring tip may be visible on a magnetic resonance image.

In an embodiment, a magnetic resonance imaging probe system can have a magnetic resonance imaging probe, having a probe shaft including a distal end and a proximal end, the probe shaft further including a core of non-magnetic material, a first insulator/dielectric covering the core, and a shield layer covering the core; a magnetic resonance imaging coil attached to the distal end of the probe shaft and including a distal end, a spring tip attached to the distal end of the imaging coil, and a connector attached to the proximal end of the probe shaft; and an interface, having a balun circuit, a decoupling circuit in electrical communication with at least one of the balun circuit and a tuning/matching circuit, the tuning/matching circuit in electrical communication with at least one of the balun circuit and the decoupling circuit, a proximal connector, in electrical communication with at least one of the balun circuit, the decoupling circuit, and the tuning/matching circuit, the proximal connector being adapted for removable electrical connection to a magnetic resonance scanner, and a distal connector, in electrical communication with at least one of the balun circuit, the decoupling circuit, and the tuning/matching circuit, the connector of the interface being adapted for removable electrical connection to the connector of the imaging probe.

In an embodiment, a device suitable for insertion into a subject can have a helical coil suitable for use as a magnetic resonance antenna, and a flexible tip coupled to a distal end of the device. In an embodiment, a method for guiding a magnetic resonance imaging probe can have providing the magnetic resonance imaging probe having a flexible tip, flexing the tip into a position suitable for advancing the probe through a structure, and advancing the probe through the structure. In an embodiment, the probe shaft can have a core of non-magnetic material, a first insulator/dielectric covering the core, and a shield layer covering the core.

In an embodiment, a magnetic resonance imaging probe may include a core of non-magnetic material, a shield layer having a distal end and surrounding at least a part of the core, a proximal spring assembly having a distal end and being coupled to the distal end of the shield layer, a joining segment attached to the distal end of the proximal spring assembly, and a magnetic resonance imaging coil attached to the segment.

In an embodiment, a magnetic resonance imaging probe may include a core of non-magnetic material, a first insulator/dielectric surrounding at least a part of the core, a shield layer surrounding at least a part of the first insulator/dielectric and having a distal end, a modified shield layer attached to the distal end of the shield layer and having a distal end, a proximal spring assembly attached to the distal end of the modified shield layer and having a distal end, a joining segment attached to the distal end of the proximal spring assembly, a magnetic resonance imaging coil attached to the joining segment and having a distal end, and a spring tip attached to the distal end of the imaging coil.

In an embodiment, a magnetic resonance imaging probe may include a core of non-magnetic material, a first insulator/dielectric surrounding at least a part of the core, a shield layer surrounding at least a part of the first insulator/dielectric and having a distal end, a modified shield layer attached to the distal end of the shield layer and having a distal end, a joining segment attached to the distal end of the modified shield layer, a magnetic resonance imaging coil attached to the joining segment and having a distal end, and a spring tip attached to the distal end of the imaging coil.

In an embodiment, a magnetic resonance imaging probe system may include a magnetic resonance imaging probe, having a probe shaft including a distal end and a proximal end, the probe shaft further including a core of non-magnetic material, a first insulator/dielectric covering the core, a shield layer covering the first insulator/dielectric and having a distal end, a proximal spring assembly attached to the distal end of the shield layer and having a distal end, and a magnetic resonance imaging coil attached to the distal end of the proximal spring assembly and having a distal end; a spring tip attached to the distal end of the imaging coil, and a connector attached to the proximal end of the probe shaft; and an interface, having a balun circuit, a decoupling circuit in electrical communication with at least one of the balun circuit and a tuning/matching circuit, the tuning/matching circuit in electrical communication with at least one of the balun circuit and the decoupling circuit, a proximal connector, in electrical communication with at least one of the balun circuit, the decoupling circuit, and the tuning/matching circuit, the proximal connector being adapted for removable electrical connection to a magnetic resonance scanner, and a distal connector, in electrical communication with at least one of the balun circuit, the decoupling circuit, and the tuning/matching circuit, the connector of the interface being adapted for removable electrical connection to the connector of the imaging probe.

In an embodiment, a device suitable for insertion into a subject may include a magnetic resonance antenna having a helical coil, and a flexible tip affixed to a distal end of the device.

In an embodiment, a method for guiding a magnetic resonance imaging probe may include providing the probe, the probe having a magnetic resonance imaging antenna and a flexible tip, inserting the probe into a structure, advancing the probe through the structure until the flexible tip encounters a first obstruction, and manipulating the probe until the flexible tip bypasses the first obstruction.

In an embodiment, the antenna may include a core of non-magnetic material, a first insulator/dielectric covering the core, and a shield layer covering the first insulator/dielectric. The core may include a Nitinol wire and alternating layers of gold, silver, and gold, surrounding at least a portion of the Nitinol wire. In an embodiment, the core may be plated with alternating layers of gold and silver.

An embodiment can further have a bare area of the core, wherein the first insulator/dielectric does not cover the bare area of the core. The antenna may attach to the probe shaft at the bare area. In an embodiment, at least part of the imaging coil surrounds at least part of the core. In an embodiment, the core can have a Nitinol wire, alternating layers of gold, silver, and gold, surrounding at least a portion of the Nitinol wire, and an insulating layer having at least one of fluoroethylene polymer, polyethylene terephthalate, or silicone, the insulating layer disposed over the alternating layers. In an embodiment, the probe shaft may be covered by alternating layers of insulator/dielectric and shielding.

In an embodiment, the core of non-magnetic material may be plated with alternating layers of gold and silver. In an embodiment, the core has a diameter in the range of about 0.004 inches to about 0.014 inches. In an embodiment, the first insulator/dielectric includes a plastic. In an embodiment, the plastic may be fluoroethylene polymer. In an embodiment, the shield layer includes Nitinol. In an embodiment, the core of non-magnetic material may be coated with a layer of fluoroethylene polymer. In an embodiment, the core of non-magnetic material may be fabricated from conductive metal having at least one of gold, silver, copper, MR-compatible stainless steel, and aluminum. In an embodiment, the core of non-magnetic material includes a super-elastic material. In an embodiment, the super-elastic material includes Nitinol.

In an embodiment, the core includes at least one of carbon, glass fiber, and a polymer, and the core may be plated with a radio frequency conductive material. In an embodiment, the core of non-magnetic material may be electrically connected to the imaging coil at least at one point. In an embodiment, the shield layer includes at least one of a braid, a paint, a deposit, a hypotube, a plating, and a sputtering. An embodiment can further have a proximal spring assembly coupled to a distal end of the shield layer.

In an embodiment, the flexible tip includes a spring. In an embodiment, the spring includes MP35N. In an embodiment, the spring may be attached to the distal end of the probe shaft by an adhesive joint. In an embodiment, the adhesive joint includes an electrically insulating material. In an embodiment, the adhesive joint electrically insulates the spring tip from the core.

In an embodiment, at least part of the imaging coil surrounds at least part of the core.

In an embodiment, the antenna includes a magnetic resonance imaging coil. In an embodiment, the imaging coil includes a helical whip with a proximate end and a distal end, the helical whip having coils with a diameter and a spacing. In an embodiment, the helical whip includes at least one of copper, gold, silver, platinum, iridium, or aluminum wire. In an embodiment, the helical whip may be covered by a biocompatible material or covering. In an embodiment, an electrical length of the helical coil may be chosen so as to compensate for the biocompatible material or covering. In an embodiment, the imaging coil has a length of up to about 12 centimeters. In an embodiment, at least one of the antenna and the flexible tip may be visible on a magnetic resonance image.

In an embodiment, the probe shaft has an outer diameter of about 0.032 inches. In an embodiment, the probe shaft has an outer diameter of about 0.014 inches. In an embodiment, the probe may be sized and shaped to be a guidewire. In an embodiment, the probe may be sized and shaped for intravascular use. An embodiment can further have a connector coupled to a proximal end of the probe shaft. The proximal end of the probe shaft can be adapted to receive a removable connector. In an embodiment, the connector is removably attached to the proximal end of the probe shaft. In an embodiment, the connector couples to an interface. In an embodiment, the interface includes at least one of a tuning-matching circuit, a balun circuit, a decoupling circuit, and a variable capacitor.

In an embodiment, at least one of the core, the shield layer, the modified shield layer, the coil, the spring tip, the proximal spring assembly, and the ribbon can include at least one of a magnetic resonance compatible material, a superelastic material, copper, gold, silver, platinum, iridium, MP35N, tantalum, Nitinol, L605, gold-platinum-iridium, gold-copper-iridium, and gold-platinum.

In an embodiment, the core can include a central core having at least one of carbon, glass fiber, and a polymer, and the core can further include a radio frequency conductive covering surrounding the central core. In an embodiment, the covering can include alternating layers of gold, silver, and gold, surrounding the central core.

In an embodiment, the antenna includes a loopless antenna. In an embodiment, the antenna includes a gold-platinum-iridium wire. In an embodiment, the wire may be shaped as a spring. In an embodiment, the probe receives a magnetic resonance signal from a sample, and the composite wire has a length substantially equal to 0.25 times the wavelength of the magnetic resonance signal when the probe is in the sample.

In an embodiment, the flexible tip includes a ribbon. In an embodiment, the ribbon includes MP35N. In an embodiment, the ribbon may be flat. An embodiment can further have a distal joint attaching the ribbon and the flexible tip. In an embodiment, the antenna may be attached to the core by at least one of an epoxy, an adhesive seal, a laserweld, an ultrasonic weld, and a solder joint. In an embodiment, the flexible tip includes round winding wire. In an embodiment, the flexible tip includes at least one of Nitinol, tantalum, MP35N, L605, gold-platinum-iridium, gold-copper-iridium, and gold-platinum. In an embodiment, the spring tip may include a ribbon. In an embodiment, a proximal portion of the ribbon may be round, and a distal portion of the ribbon may be flat. In an embodiment, the distal end of the ribbon may be flat-dropped. In an embodiment, the spring tip may include at least one of round winding wire and flat winding wire.

In an embodiment, an outer surface of the probe shaft may be insulated with a biocompatible material or coating. An embodiment can further have a cover layer covering at least a portion of the probe shaft. In an embodiment, the cover layer includes at least one of polyethylene terephthalate and silicone. An embodiment can further have a lubricious coating covering at least a portion of the cover layer.

In an embodiment, the proximal spring assembly may be attached to the distal end of the shield layer by at least one of a conductive epoxy, an adhesive seal, a laserweld, an ultrasonic weld, and a solder joint. In an embodiment, the proximal spring assembly includes a magnetic resonance compatible material. In an embodiment, the proximal spring assembly includes at least one of Nitinol and tantalum. In an embodiment, the proximal spring assembly includes a round winding wire. In an embodiment, the round winding wire may be stacked. An embodiment can further have a spring tip attached to a distal end of the imaging coil. In an embodiment, the probe shaft has an outer diameter in the range of about 0.010 inches to 0.5 inches. In an embodiment, at least one of the probe shaft, the imaging coil, and the spring tip may be visible under fluoroscopy.

In an embodiment, the tuning-matching circuit includes a capacitor and an inductor in parallel with the capacitor. In an embodiment, the tuning-matching circuit matches the interface to an input impedance in the range of about 20 to 80 ohms, preferably 50 ohms. In an embodiment, the capacitor has a value of 22 picoFarads, and the inductor has a value of 198 nanoHenrys. In an embodiment, the interface includes a balun circuit. In an embodiment, the balun circuit includes an inductor coil and a capacitor, the capacitor connecting a case of the interface to ground. The inductor and capacitor can be tuned to the magnetic resonance imaging frequency. In an embodiment, the inductor coil includes a semirigid coax, and the capacitor has a value of 39 picoFarads.

In an embodiment, the interface includes a decoupling circuit. In an embodiment, the decoupling circuit includes a capacitor and a diode in parallel with the capacitor. In an embodiment, the capacitor has a value in the range from about 50 picoFarads (pF) to about 500 pF, preferably about 100 picoFarads, and the diode may be a PIN diode.

In an embodiment, the antenna includes a composite wire. In an embodiment, the spring has a pitch in the range of about 0.004 inches to about 0.015 inches. An embodiment can further have a second insulator/dielectric. In an embodiment, the core of non-magnetic material may be plated with a plurality of metal layers. In an embodiment, at least one of the plurality of metal layers includes a precious metal. In an embodiment, the diameter may be about 0.0085 inches. In an embodiment, the core includes a distal tip, and a diameter of the core tapers toward the distal tip. In an embodiment, the shield layer includes a Nitinol hypotube. In an embodiment, the Nitinol hypotube has a diameter of in the range of about 0.014 inches to about 0.035 inches. In an embodiment, the Nitinol hypotube may be heat treated. In an embodiment, the shield layer includes a proximal end, and about 2 centimeters of the proximal end of the shield layer may be gold-plated.

In an embodiment, the distal joint seals a distal end of the spring tip. In an embodiment, the winding wire may be round. In an embodiment, the winding wire may be stacked. In an embodiment, the winding wire has a diameter in the range from about 0.001 inches to about 0.005 inches. In an embodiment, the diameter may be about 0.0003 inches. In an embodiment, the spring tip includes a magnetic resonance-compatible material.

In an embodiment, the core of non-magnetic material may be plated with a plurality of layers of conductive metal, the layers of conductive metal having at least one of gold, silver, platinum, copper and aluminum. In an embodiment, the core of non-magnetic material may be plated with alternating layers of gold and silver. In an embodiment, the core of non-magnetic material may be plated with a plurality of layers of conductive metal, the layers of conductive metal having at least one of gold, silver, copper and aluminum. In an embodiment, the core of non-magnetic material includes a non-metallic material plated with a radio frequency conductive material.

In an embodiment, the helical whip may be electrically connected to the core at least at one point. In an embodiment, the portion extends from the proximal end of the probe shaft to the distal end of the imaging coil. In an embodiment, an epoxy adhesive seals the imaging coil, the core, and the cover layer. In an embodiment, at least one of the imaging coil and the spring tip may be visible on a magnetic resonance image. In an embodiment, the proximal end of the probe shaft may be adapted for quick removal of the connector, and the connector may be adapted for removability.

BRIEF DESCRIPTION OF THE DRAWINGS

Other objects, features, and advantages of the disclosed systems, devices, assemblies, probes, and methods will be apparent from the following detailed description of the preferred embodiments as illustrated in the accompanying drawings, in which reference characters refer to the same parts throughout the various views. The drawings are not necessarily to scale, emphasis being placed upon illustrating principles of the disclosed systems, devices, assemblies, probes, and methods.

FIGS. 24 and 25 show different views of an embodiment including a vice-like connector between the connector portion and the mated connector portion and allow the guidewire to rotate within the connector.

FIG. 32 shows in more detail an embodiment of an imaging probe.

FIG. 33 shows in more detail an imaging coil and flexible tip assembly.

FIGS. 34A-C show cross-sections of an interface box.

FIGS. 34 D-E show external views of an interface box.

DETAILED DESCRIPTION

Figure 1:
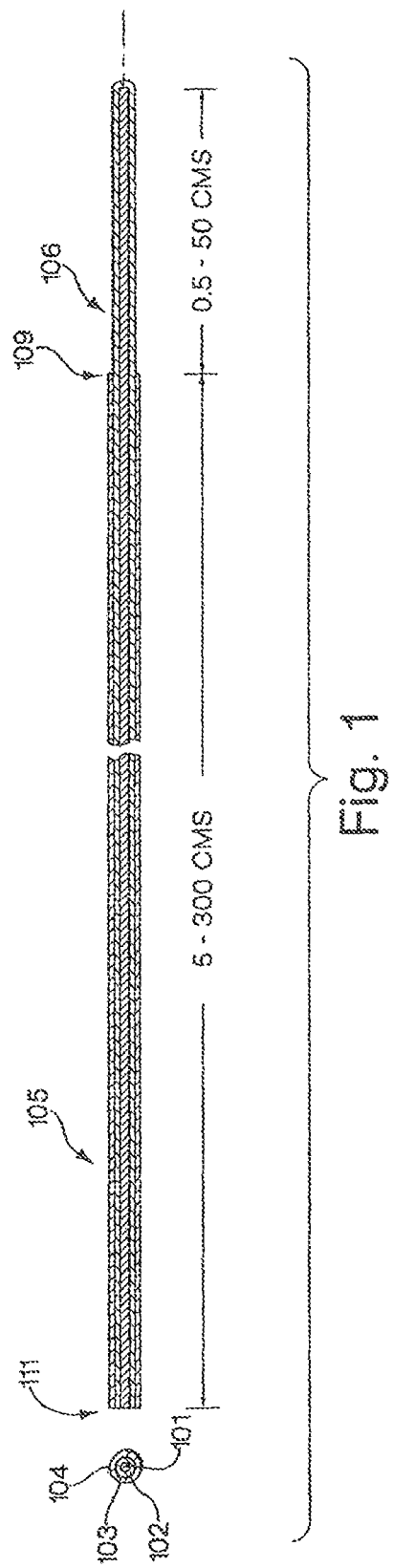
FIG. 1 shows a cross-sectional side and end view illustrating the structure of a guidewire probe with a linear whip antenna according to the disclosed systems, devices, assemblies, probes, and methods.

Herein is disclosed a loopless whip antenna for use as or with an imaging probe that is suitable for vascular procedures on human subjects in a conventional MRI machine designed for medical use. This description does not, however, limit the scope of the disclosed systems, devices, assemblies, probes, and methods. In particular, the disclosed systems, devices, assemblies, probes, and methods can have a wide variety of probes and MRI antennas whether a whip antenna or not and whether of looped, loopless or of other design which is suitable for use as an imaging probe as is understood in the art. The subject of the disclosed systems, devices, assemblies, probes, and methods is also not limited to human beings but can be used on a variety of subjects where the use of an imaging probe is desired. These include but are not limited to, applications of the probe in the body or portion of the body of any human, non-human animal, or other biological organism, living, deceased or otherwise; applications involving placement of the probe in any fluid, gel, solid, gas, plasma or other state of matter where the use of an imaging probe is desired in that matter, placing the probe in the vicinity of a portion of a subject for the purpose of viewing that portion of that subject through the probe's proximity, or guiding a device to within that portion's proximity; the use of a probe to simultaneously guide an interventional device and image the area on which the interventional device is to be used; or any of the previous in any combination.

As used herein, the term imaging probe is understood to include any device insertable into the subject of an intervention that provides MR images of an anatomic area internal to that subject. For example, an imaging probe may be configured to be insertable into a vascular structure, as described below in more detail. An imaging probe for intravascular use may produce images of the vascular structure within which it is situated, and may further provide images of tissues surrounding the vascular structure. These images may be used for further diagnostic or therapeutic purposes. In one embodiment, an imaging probe may be dimensionally adaptable to permit the direction of other interventional tools along it or over it. When used as a guide for other interventional tools, whether diagnostic or therapeutic, the imaging probe may be termed an imaging guidewire. As described below at greater length, in one embodiment an imaging guidewire may be combined with a variety of interventional tools in the performance of diagnostic or therapeutic procedures, as will be appreciated by those of ordinary skill in the art.

The disclosed systems, devices, assemblies, probes, and methods are also not limited to a conventional MRI machine used medically but can be used in any type of scanning device that can measure magnetic resonance. Therefore, we use the term MRI machine to apply to any type of machine, device, system, means, or process which allows the detection of magnetic resonance in any type or state of matter, such device being currently known or later developed, whether for use on humans, non-human animals, other biological organisms, biological tissues or samples, or inorganic matter. Such an MRI machine may be of any shape and for scanning any size subject or portion of a subject.

The application of guidewires is also not limited to vascular interventions. Guidewires are commonly used in many non-vascular applications for the placement of various probes and catheters into the gastrointestinal (GI) tract, the biliary duct, the urethra, bladder, ureter and other orifices or surgical openings. The disclosed systems may be adapted to a plurality of minimally invasive applications. Guidewires according to the present disclosed systems, devices, assemblies, probes, and methods may, in certain embodiments, be used for passage into and through the upper airway, trachea and bronchial tree. Examination of these structures using the disclosed systems, devices, assemblies, probes, and methods may be performed to detect abnormalities of the lungs or tracheobronchial tree, ideally at an early stage for early treatment. As an example, the early detection of a pre-malignant lesion in the tracheobronchial tree could permit early extirpation before an invasive cancer develops; even if an invasive cancer is detected, it may be possible to detect and treat these lesions at their earliest stages, before lymph node invasion or distant metastasis. Similarly, the disclosed systems, devices, assemblies, probes, and methods are applicable to any body lumen or body cavity wherein early detection of pre-malignant and malignant disease is desirable. As examples, these systems and methods could be used for the evaluation of the esophagus, stomach and biliary tree to identify neoplasms and to distinguish benign from malignant tissue proliferation. As examples, these systems and methods could be used for the evaluation of the colon and rectum to identify abnormalities and malignancies. These systems and methods could also be used for the evaluation of the male and female urogenital systems, including bladder, urethra, prostate, uterus, cervix and ovary, to identify therein abnormalities and malignancies.

Further, the diagnostic function of the MRI would be useful in the evaluation of any mucosal malignancy to identify how far through the wall of the affected organ the malignancy has invaded. It is understood in the art that extent of invasiveness into and through the wall, diagnosable by MRI, is an important characteristic of an intraluminal cancer.

The diagnostic function of the MRI, as the probe is guided to the target tissue, may be combined with therapeutic interventions. For example, a small lesion found within a body lumen using the disclosed systems, devices, assemblies, probes, and methods may be suitable for localized ablation, wherein the lesion's response to the delivery of radio frequency energy or other ablative energy can be monitored in near real time by the high resolution MRI as disclosed herein.

The scale of the devices described herein may be dimensionally adaptable to a number of body cavities and lumens traditionally inaccessible to interventive methods known in the art. For example, the eustachian tube, the nasal airways and the craniofacial sinuses may all be accessible to a probe designed in accordance with the present disclosure. Using one of these orifices as an entryway into the craniofacial skeleton may permit the diagnosis or evaluation of a variety of otolaryngological and neurological conditions with greater precision than is currently available using whole-patient CT or MRI. As an example, transsphenoid evaluation of intracranial or sellar lesions may be possible. The imaging of these lesions provided by the disclosed systems, devices, assemblies, probes, and methods may be combined with therapeutic techniques for extirpating or otherwise treating the lesion using minimally invasive technologies. For example, an aneurysm of the Circle of Willis that is identified using high-resolution MRI may be suitable for clipping under MRI control using minimally invasive techniques. As another example, a pituitary tumor can be evaluated for its extensiveness using these systems and methods, and its resection can be precisely monitored. Use of these systems and methods may also permit diagnosis of abnormalities in organs considered inaccessible to traditional monitoring methods. For example, the pancreas may be examined, using an embodiment of the disclosed systems, devices, assemblies, probes, and methods, permitting the early diagnosis of pancreatic lesions. As another example, embodiments of the disclosed systems, devices, assemblies, probes, and methods may be adapted for intracranial use, for the diagnosis of lesions of the central nervous system or for precise anatomic delineation thereof. Ablative techniques may be combined with these diagnostic modalities to permit treatment of abnormalities using embodiments of the disclosed systems, devices, assemblies, probes, and methods to help determine the extent of the pathology and to monitor the effectiveness of the ablation in removing the abnormality. Trigeminal neuralgia is an example of a condition where delineation of the relevant intracranial anatomy is vital for the identification of the neuroanatomical structures to be ablated or treated. MRI using the disclosed systems, devices, assemblies, probes, and methods may usefully help direct the surgeon to the precise tissues requiring treatment.

Conventional minimally invasive techniques such as laparoscopy, thoracoscopy, mediastinoscopy, and arthroscopy may all be combined with these systems and methods to permit more accurate identification of target lesions and to monitor therapies directed at the target lesions. MRI guidance according to these systems and methods may be particularly valuable in determining the extensiveness of a lesion that is to be resected or biopsied. For example, in mediastinoscopy, it may be difficult to distinguish between large blood-filled vessels and pathological lymph nodes, the latter being the target for the biopsy being performed. The operator performing the procedure must sample the pathological lymph nodes without damaging the large vessels in the area, an inadvertancy that can result in profound, even exsanguinating hemorrhage. MRI guidance according to these systems and methods can not only distinguish among the various types of anatomic structures, but also can map out the extent of lymph node involvement and direct the operator towards those lymph nodes most likely to bear the abnormal tissue being sought. A number of applications will be readily apparent to practitioners of ordinary skill in the art, whereby a conventional endoscopy procedure combined with these systems and methods will permit the diagnostic evaluation of a tissue or organ within a body lumen or a body cavity. The intraperitoneal space, for example, may be usefully evaluated using these systems and methods, with access to this space being provided by laparoscopic instrumentation, and with MRI being used to approach and identify target tissues. Intraperitoneal diagnosis using these systems and methods may be helpful in diagnosis of various retroperitoneal lymphadenopathies, such as those indicative of lymphoma, or such as those indicative of spread from a malignant melanoma of the lower extremity. Other examples may be evident to ordinarily skilled practitioners in the medical arts.

Combining these systems and methods with other diagnostic modalities may permit better or earlier diagnosis of malignancies. For example, use of contrast agents in addition to the systems and methods described herein may permit identification of tumors on the basis of their abnormal blood flow or metabolism. Contrast agents or other markers carried by body fluids may permit these systems and methods to be used for diagnosis of abnormal bleeding sites, such as occult gastrointestinal bleeding points or bleeding varices, situations where direct visual inspection of the lesion may have limited diagnostic or therapeutic value.

It is understood that advances in fabrication of static MRI machines will permit more localized anatomic evaluation of specialized body parts, and further will permit easier access to the patient for interventional techniques. These developments may permit the disclosed systems, devices, assemblies, probes, and methods to be used as a replacement for various ultrasound-guided techniques such as fertility procedures. In certain embodiments, the disclosed systems, devices, assemblies, probes, and methods may be adapted for screening procedures using probes dimensionally adapted for appropriate bodily orifices. For example, these systems and methods may be useful in identifying and determining extensiveness of gynecological cancers, including cervical cancer, uterine cancer and ovarian cancer. Other applications should become available to practitioners of ordinary skill in the art with no more than routine experimentation.

The probe of the disclosed systems, devices, assemblies, probes, and methods can be described and understood as having multiple different forms of antenna whip and design. The first of which is depicted in FIG. 1 wherein the probe has a linear whip antenna 106.

Figure 2:
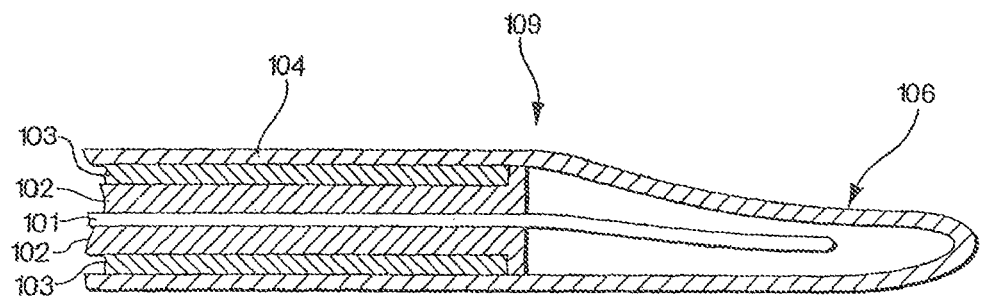
FIG. 2 shows a cross-sectional side view illustrating the structure of one potential shielded linear whip antenna according to the disclosed systems, devices, assemblies, probes, and methods.
Figure 3:
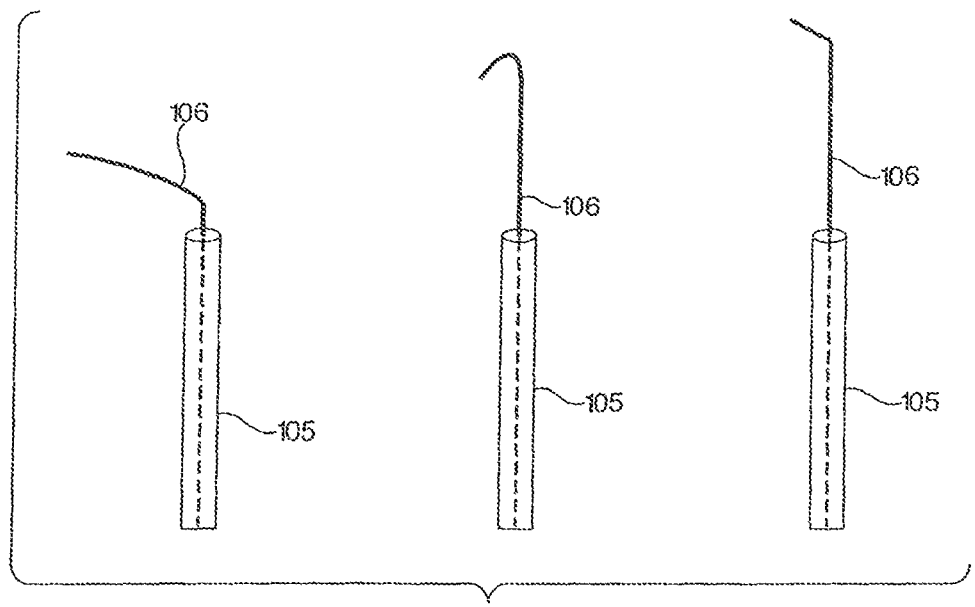
FIG. 3 shows three potential alternate shapes for a linear whip antenna.

The whip refers to the antenna at the end of the probe which is a whip antenna. In this case the whip has a primarily unbent protrusion and is therefore called a linear whip antenna 106. The probe preferably has a probe shaft 105 with a distal end 109 and a proximate end 111. The probe shaft can have multiple layers of different materials including a core 101 having at least one first electrically conducting component, a first insulator/dielectric 102 for providing insulation, a shielding 103 having at least one second conducting component, and an optional second insulator/dielectric 104 as shown in FIG. 2. The linear whip antenna 106 extends from the distal end 109 of the probe shaft 105. It would be understood that a linear whip antenna 106 does not have to be straight but may have a curve or slight hook at the end as is understood in the art to facilitate engagement of the device into complex vessels as shown in FIG. 3. In one embodiment of the disclosed systems, devices, assemblies, probes, and methods, it would be understood that the linear whip antenna 106 could be flexible or could be bent to form non-linear shapes as the probe was twisted through complicated pathways within the subject. In an alternative embodiment the linear whip antenna can have a ribbon or paddle shape such as those shown in FIG. 16.

The core 101 can have a super-elastic material such as the Tinol® range of materials (also known as Nitinol or NiTi). Super-elastics generally have a titanium-nickel alloy and have many positive attributes for use as a base for the probes of the disclosed systems, devices, assemblies, probes, and methods. The MR properties of Nitinol are favorable due to the visibility with limited artifact. Super-elastics may be significantly deformed and still return to their original shape. Such deformation and "shape memory" can take place through actions based on changes in temperature. Super-elastic materials are also known for high biocompatability and show good properties for use within biological organisms or matter. Super-elastics in the antenna designs of the disclosed systems, devices, assemblies, probes, and methods could be of a variety of shapes including wire, ribbon, microtubing, sheets or any other form as is known to the art and can have Nitinol wire that can be plated with layers of gold-silver-gold, or layers of gold, silver or copper applied either singly or in combination. The core 101 can alternatively have different materials, including, but not limited to, MR-compatible stainless steel, other metallic materials that are non-magnetic, non-metallic substances such as carbon, glass fiber, or polymer, that can be plated with a layer of a good RF conductor such as copper, silver, or gold either singly or in multiple layers, or any of the previous in any combination. In the case of an aluminum core 101, the surface can be readily oxidized as is known to the art to provide the first insulator/dielectric 102.

The first insulator/dielectric 102 and the second insulator/dielectric 104, may have any insulator/dielectric as is known to the art including any polymer, such as, but not limited to, an elastomeric grade PEBAX, Nylon, Teflon®, polyurethane, fluoroethylene polymer (FEP), or polyvinylidene fluoride (PVDF), or any combination of polymers with appropriate electrical properties. The insulator/dielectric could also have aluminum oxide or any other nonpolymeric element or compound as would be understood by one of skill in the art.

The thickness of the first insulator/dielectric 102 and the second optional insulator/dielectric 104 can be determined so as to control the impedance of the cable formed. The impedance can be in the range of 150 ohms to 10 ohms. The wire can have a uniform impedance throughout the length or the impedance can vary with length, for instance, by having low impedance closer to the proximate end 111 as compared to the distal end 109.

The shielding layer 103 may have any MR-compatible conductive material including, but not limited to, copper plated with silver, copper plated with gold, Nitinol plated with gold, conductive inks, conductive coatings or any of the previous in any combination. The shielding can be in the form of a braid, a mesh, or a continuous tubing such as, but not limited to, a gold-silver-gold plated Nitinol hypotube. The shielding can be continuous or coiled toward the distal end 109 and can extend beyond the distal end 109 of the probe shaft 105 or may be discontinued at the distal end 109 of the probe shaft 105. Discontinuing the shielding can create a stronger signal from the antenna, but may create detrimental effects when the probe is used in a human body.

Figure 4:
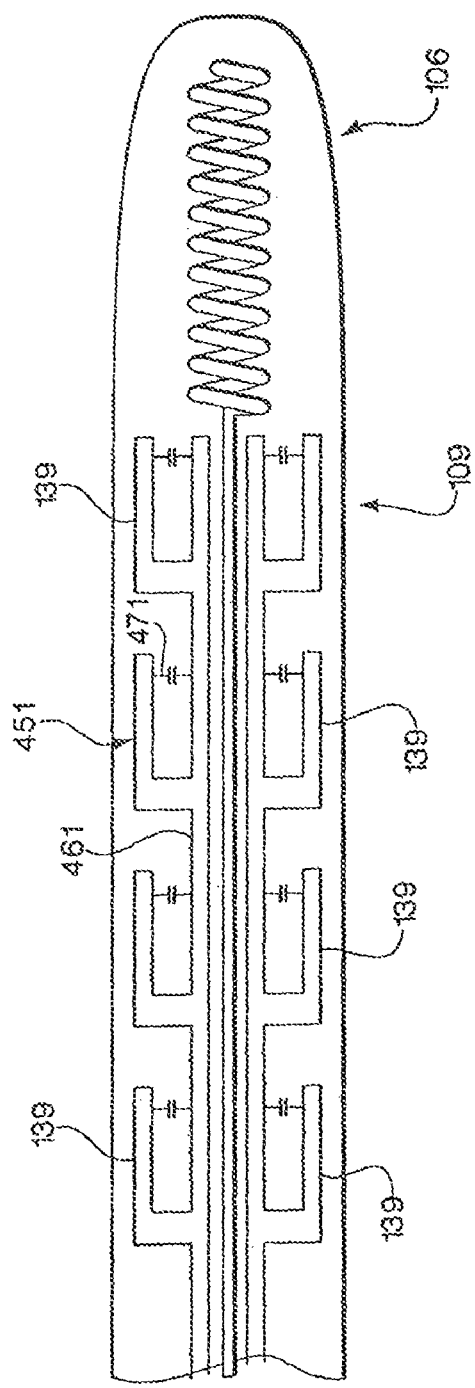
FIG. 4 shows a potential embodiment of the disclosed systems, devices, assemblies, probes, and methods wherein the shielding includes a series of balun circuits.

To increase the safety and the signal-to-noise ratio of the antenna, the shielding 103 can be added to the probe shaft in the form of a balun circuit as is understood in the art. This reduces the effect of induced currents due to external RF and magnetic fields. The tertiary shielding 451 can be continuous or discontinuous. It can have capacitors connecting the discontinuous sections or it can be connected directly to the primary shielding 461 or connected to the primary shielding 461 with capacitors 471 or by any other method understood in the art, or by a series of balun circuits 139 as shown in FIG. 4.

In another embodiment of the disclosed systems, devices, assemblies, probes, and methods, a balun circuit is placed on the probe in a tuned form (also known as a bazooka circuit) as is known to the art. This tuned balun circuit could help to increase the SNR performance and reduce the induced currents on the wire during an RF pulse transmission by any external RF coil (such as the transverse magnetic field in an MRI machine). This circuit may also decrease the risk of possible excessive Ohmic heating from the presence of the probe inside the body.

The second optional insulator/dielectric 104 is desirable over the antenna whip as depicted in FIG. 2 so as not to insert a straight cylindrical segment of bare wire into the patient with direct blood and tissue contact. The problem with this solution, however, is that the optimal length of the whip portion of the device is determined based upon the operating electromagnetic wavelength in vivo which in turn depend upon the effective dielectric constant as experienced by the antenna. For the case of a bare wire loaded in water, this length is approximately 4-12 cm, which represents a reasonable length for in vivo use. The addition of a second insulator/dielectric 104 to the outer surface of the antenna however, decreases the effective dielectric constant, which in turn increases the operating wavelength and thus the optimal whip length from 4-12 cm to 30-100 cm for a dielectric with a dielectric constant of about 2 to 4. As it is clear that a 30-100 cm antenna whip may be prohibitively long for some in vivo use, an alternative insulated whip design could be desired when the antenna is insulated as is discussed below. In addition, covering the antenna with a second insulator/dielectric 104 increases the diameter of the antenna making it increasingly difficult to insert in small vessels. In one embodiment, the linear whip antenna 106 has the narrowest possible diameter to allow such insertion.

A typical assembly procedure for an MRI probe according to one of the disclosed systems, devices, assemblies, probes, and methods can involve the following steps. First, the first insulator/dielectric 102 is attached to a gold-silver-gold plated Nitinol core 101. This can be done by means of extrusion, drawing, a heat shrink tubing, or any other method known to the art. Next, the shielding 103 is loaded on the assembly leaving a portion of the assembly exposed to act as the linear whip antenna 106. This can be done by means of braiding, plating, painting, a hypotube, sputtering, or any other means known to the art. Alternatively, a metallic hypotube can be used instead of braiding to add mechanical stiffness to the probe shaft. Lastly, the second insulator/dielectric 104 is loaded on the probe shaft 105. A connector can then be attached to the proximate end 111 of the probe shaft 105 to facilitate connecting to the interface circuitry to be connected to the MRI scanner. The connector can be any type as is known to the art, or could alternatively be any of the connectors described below. In a further embodiment according to a disclosed system, device, assembly, probe, or method, the connector can be replaced by mechanical forming of the proximal tip to enable attachment of a snap-fit connector or by any other means of connections or termination of the probe as would be known to one of skill in the art. An optional coating of lubricant may further be added to the probe shaft 105 and/or antenna whip to reduce drag.

The disclosed systems, devices, assemblies, probes, and methods contemplate the manufacture of the linear whip antenna 106 and probe shaft 105 as a single piece as is described above. Alternatively, the probe shaft 105 and linear whip antenna 106 could be constructed as two separate pieces and attached together by any means known to the art either permanently (including, but not limited to, use of welding, soldering and/or electrically conducting glue or epoxy) or removeably (including, but not limited to, a snap-on or locking connection).

Figure 5:
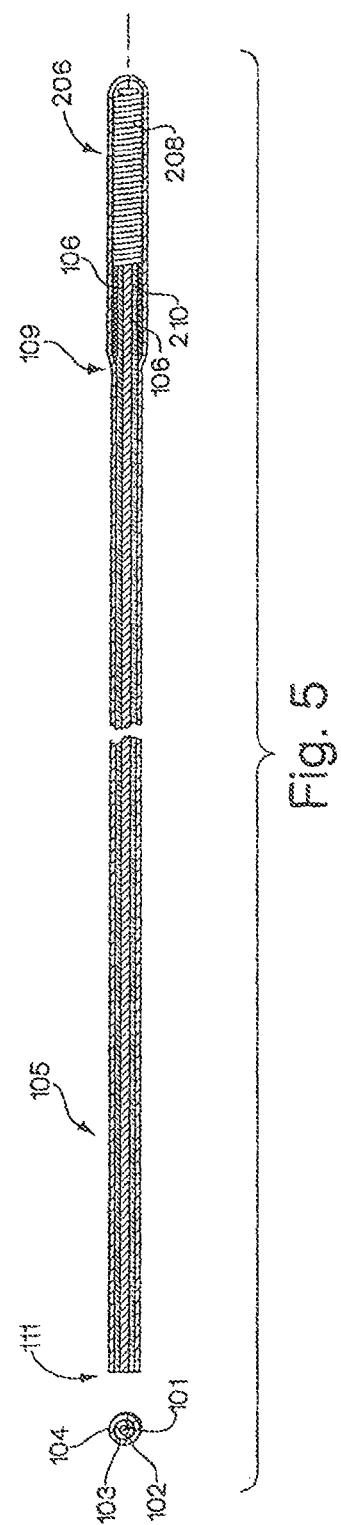
FIG. 5 shows a cross-sectional side and end view illustrating a guidewire probe according to an embodiment of the disclosed systems, devices, assemblies, probes, and methods wherein the antenna whip includes a combination whip where a helical coil may be connected to a linear whip antenna at multiple points.
Figure 6:
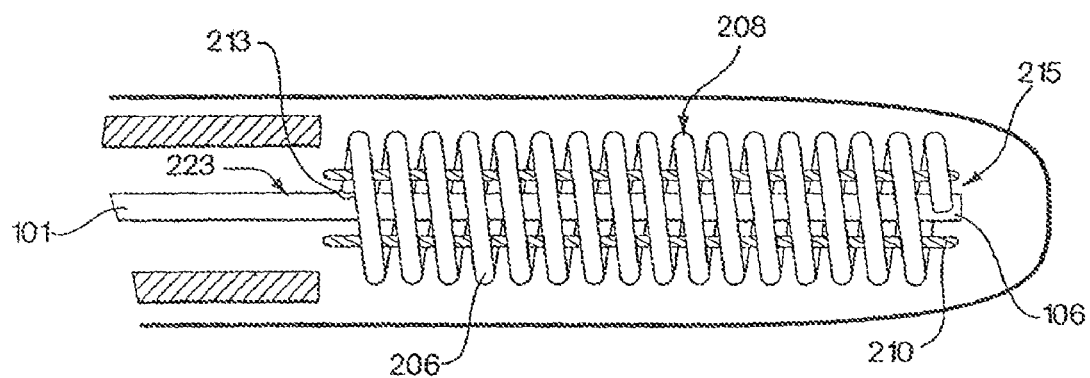
FIG. 6 shows an embodiment in which a helical coil electronically connected to a linear whip antenna at a single point.
Figure 7:
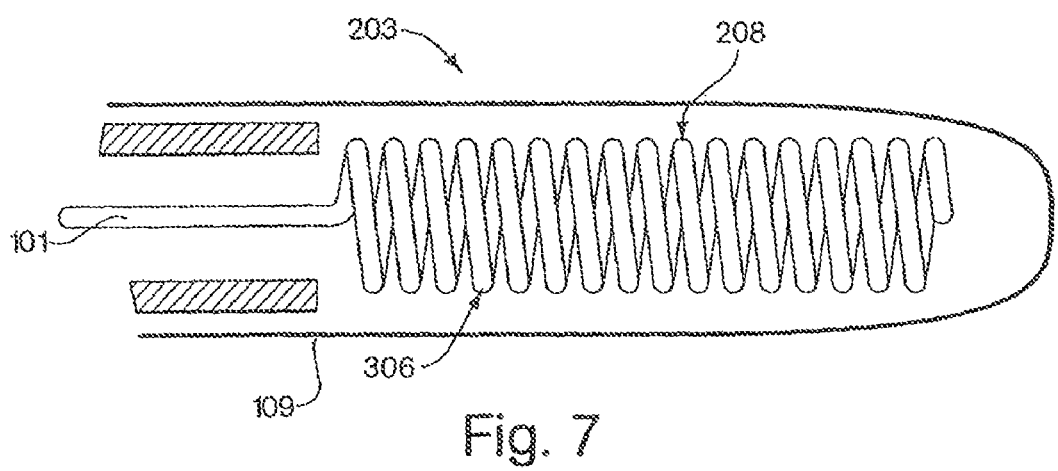
FIG. 7 shows an embodiment in which a helical coil alone includes a helical whip antenna.

FIGS. 5, 6 and 7 show alternative embodiments of the disclosed systems, devices, assemblies, probes, and methods using a helical coil antenna that obtains through its shape the ability to be the same physical length as a linear whip antenna, while still maintaining the electrical length of a much longer linear whip and therefore having desirable properties even when shielded by a second insulator/dielectric 104. FIGS. 5 and 6 show a combination whip antenna 206 where a helical coil is placed over and electrically joined to a linear whip antenna 101. FIG. 7 shows a guidewire probe with a helical whip antenna 206 where the helical coil 208 has the antenna alone.

Helically coiling the antenna shortens the physical antenna length while still producing optimum performance. Covering the antenna with an insulator, increases the optimum antenna length because the insulator effects the ability of the antenna to detect signal. In this case, coiling the antenna can be used to compensate for this increase in optimum antenna length. That is, a coil of wire can have a longer piece of wire in a shorter physical form.

A helical coil antenna has further mechanical advantages over a linear antenna. In particular, a coil is flexible and "springy" allowing it to navigate through complicated biological pathways without bending, kinking, or breaking, as opposed to a linear antenna which can have many of these problems since it is narrow and may have poor mechanical properties. Therefore, in one embodiment of the disclosed systems, devices, assemblies, probes, and methods, the helical coil is placed over a linear antenna, not necessarily to change signal, but to "superimpose" preferred mechanical properties on the linear antenna as exemplified in FIG. 8.

The helical coil also provides for detection of magnetic resonance in multiple directions. The signal received by a linear antenna is dependent upon the orientation of the antenna with respect to the main magnetic field as is known to the art. When a linear antenna design becomes bent or changes geometric planes, the sensitivity of the antenna and thus image quality can be degraded, with zero signal detected in some cases.

As diagnostic and therapeutic catheter interventions inherently involve movement of the catheter in planes transverse to the main longitudinal axis of the body, and therefore transverse to the magnetic fields in the MRI machine, an antenna design capable of removing this orientation dependency could be desirable in many cases. The unique physical geometry of the helical coil antenna allows detection of radio frequencies from two orthogonal components of the processing transverse magnetization, which is known as quadrature detection. Quadrature designs are able to create a circularly polarized electric field that results in a 50% reduction in RF power deposition and up to a 40% increase in signal to noise ratio. The total polarization field (E) of a N turn normal mode helical antenna is:

$$E = a_\theta E_\theta + a_\phi E_\phi = \frac{N\omega I_o}{4\pi\varepsilon_o c^2} \frac{e^{-j\beta r}}{r} [a_\theta jD + a_\phi \beta A]\sin(\theta) \quad (1)$$

where: $E_\theta$ and $E_\phi$ are the electric fields produced by a small loop and short dipole respectively, N=number of turns, $I_0$=initial current, c=speed of propagation, $\varepsilon_0$=permittivity constant, β=wave number, D=coil diameter. Note that the $E_\theta$ and $E_\phi$ components are in both space and time quadrature, resulting in an elliptical polarization field. In addition to these very important advantages, such a design allows the imaging capabilities of the device to be independent of spatial orientation and therefore it can be used in any vessel or other area in the body.

Figure 10A:
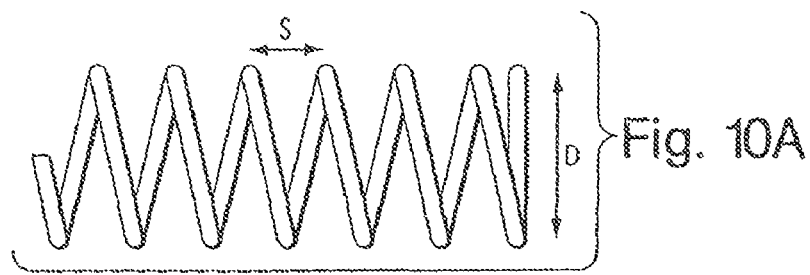
FIG. 10 shows a representation of the receiving properties of a helical coil antenna.
Figure 10B:
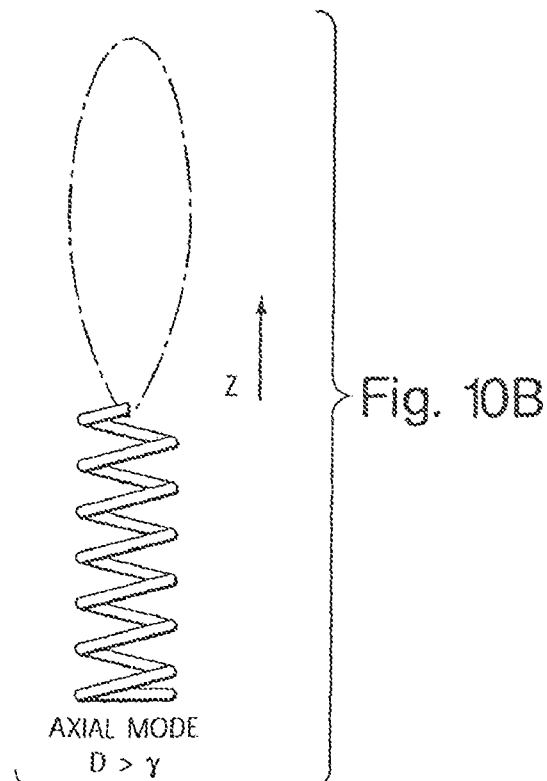
Figure 10C:
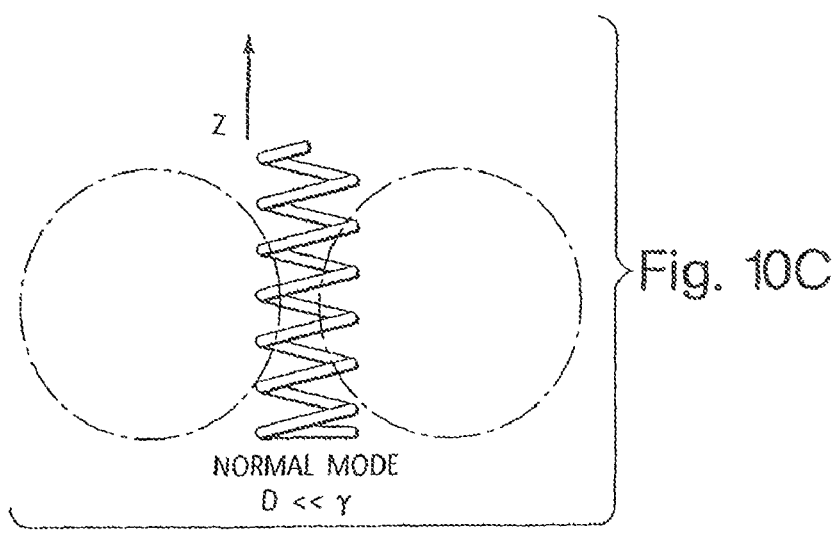

Helical coil antennas have two distinct and very different operating modes depending upon, as shown in FIG. 10, the physical dimensions of the windings and speed of wave propagation through the medium. When the diameter(D) and spacing(S) between the windings is comparable to the wavelength 1 of the RF MRI signal to be detected with the coil inserted in the subject, (Dλ=Sλ=1, where Dλ=helix diameter, Sλ=coil spacing), the helical coil antenna operates in an end fire or axial mode, where polarization occurs primarily along the axis of the helix as depicted in FIG. 10(b). This is similar to the operation of the linear antenna. When Dλ and Sλ are much smaller than λ, the helical antenna is said to operate in normal mode where polarization occurs orthogonal or broadside to the helical axis as shown in FIG. 10(c) and described in equation (1). Since the RF frequencies used in MRI tend to be very long, normal mode operation is the standard for a probe of the disclosed systems, devices, assemblies, probes, and methods.

Figure 8:
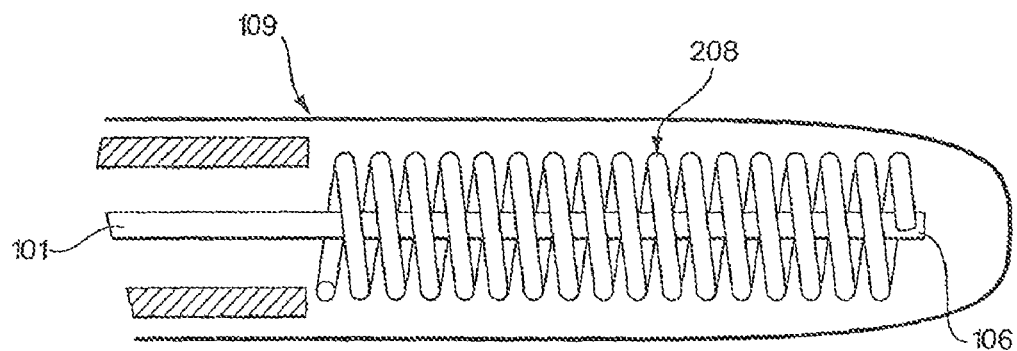
FIG. 8 shows an embodiment in which a helical coil may be placed over a linear whip antenna without making an electrical connection between the two.

FIGS. 5 and 6 show a probe with a helical coil 208 on top of a linear whip antenna 106. This creates a combination whip antenna 206. In one embodiment of the disclosed systems, devices, assemblies, probes, and methods, there can be an electrical connection between the linear whip and the helical coil in one point 213 as shown in FIG. 5 or multiple points as shown in FIG. 6. Alternatively, the connection point could be at the distal end 215 of the linear whip antenna 106 instead of at the proximate end 223 as shown in FIG. 6. This allows for both portions to act as antennas and can produce an antenna with higher SNR without increasing physical size significantly. A thin insulator 210 may be placed between the linear whip antenna 106 and the helical coil 208 in any combination antenna 206. In another embodiment of the disclosed systems, devices, assemblies, probes, and methods (FIG. 8), the helical coil 208 and the linear whip antenna 106 are not electrically connected to one other. In this embodiment, the helical coil 208 provides beneficial mechanical properties to the linear whip antenna 106. In particular, it can make the linear whip antenna 106 more rugged and more flexible allowing for better mechanical properties within the subject. In FIGS. 5, 6 and 8, the probe shaft 105 can be built similarly to the probe shaft of FIG. 1 and all listed materials for the probe of FIG. 1 are also available for the probe of FIGS. 5, 6, and 8. This type of construction is not limited to these figures. Any probe shift 105 in any embodiment herein described may be constructed in a similar manner. In assembly, the helical coil 208 can be added to a preconstructed probe with a linear whip antenna 106. The addition can either complete the electrical connection to the helical coil 208 or not depending on the desired final probe. Alternatively the probe can be manufactured with the helical coil 208 already attached to the probe in any configuration.

Figure 9:
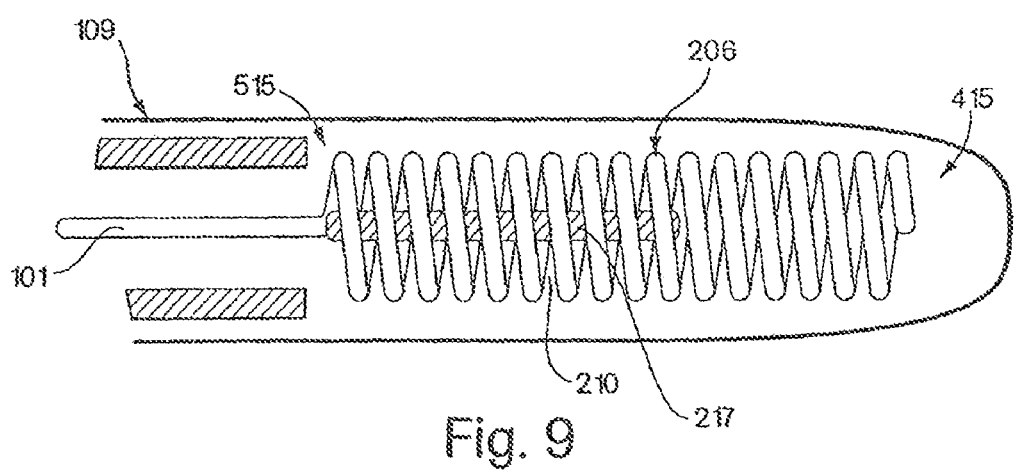
FIG. 9 shows an embodiment in which a core may be present inside a helical whip antenna.

In FIG. 7, the helical coil 208 has the entire helical coil whip antenna 306. In this depiction the helical coil 208 is electrically connected to the core 101 of the probe shaft 105. In this case, there is no linear whip antenna 106. Therefore, in another embodiment of the disclosed systems, devices, assemblies, probes, and methods, the whip is entirely helically coiled. This configuration can provide advantages in mechanical properties. In particular, the helical coil whip antenna 306 can be physically shorter or narrower than the combination whip antennas 206 depicted in FIGS. 5, 6, and 8 without significant loss of electrical length. In addition, since the helical coil whip antenna 306 has no linear portions and is only coiled, it is more flexible than any of the other antennas allowing it to turn sharper corners in the subject. Finally, the helical coil whip antenna 306 is more deformable than any of the previous antenna designs which makes the antenna less likely to puncture vessel walls. If desired, the flexibility of this antenna can be adjusted by including a core component 217 attached to the distal end 109 of the probe shaft 105 if non-conducting or unattached if conducting, as shown in FIG. 9. Core 217 need not extend to the distal end 415 of the helical coil whip antenna 306.

Figure 11:
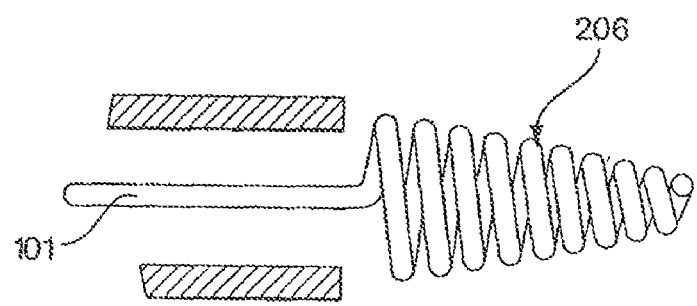
FIG. 11 shows a potential embodiment of a helical whip antenna where the diameter of the coils decreases from the proximate to the distal end of the helical whip antenna.
Figure 12:
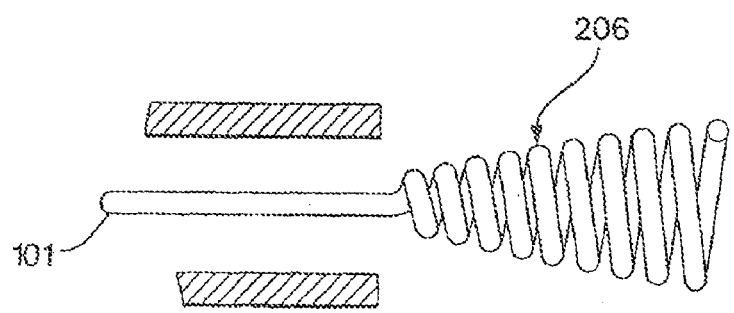
FIG. 12 shows a potential embodiment of a helical whip antenna where the diameter of the coils increases from the proximate to the distal end of the helical whip antenna.
Figure 13:
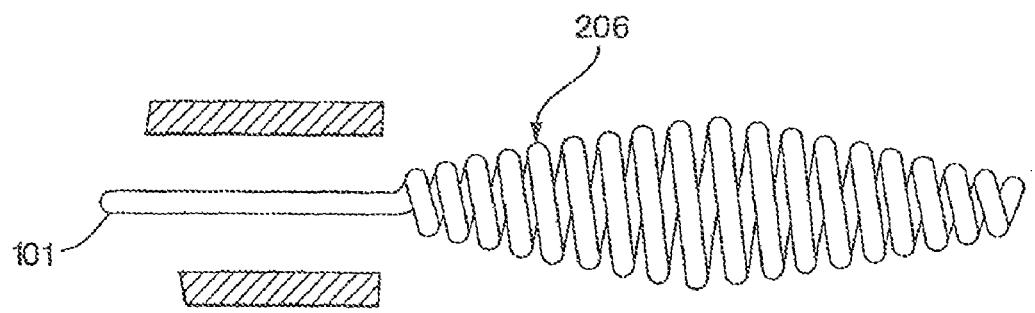
FIG. 13 shows a potential embodiment of a helical whip antenna where the diameter of the coils varies along the length of the helical coil antenna.
Figure 14:
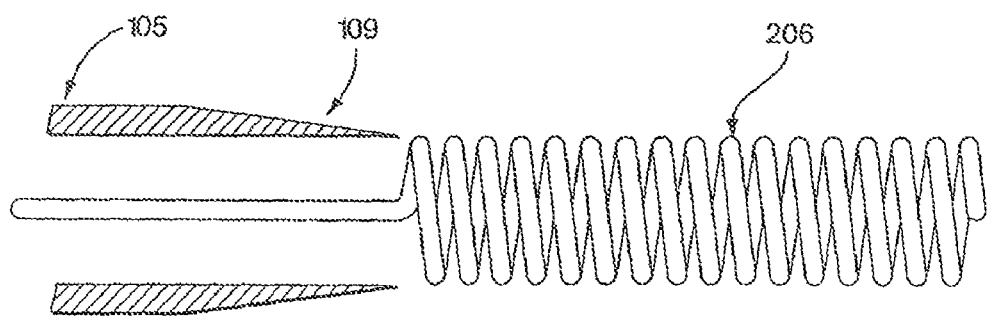
FIG. 14 shows an embodiment in which the probe shaft decreases in diameter at its distal end.

FIGS. 11, 12 and 13 depict alternative embodiments of the helical coil whip antenna 306 that can be used in place of the whip designs shown in FIGS. 7 and 9. In FIG. 11, the helical coil whip antenna 306 has been tapered with decreasing diameter towards the distal end 415 to vary the flexibility of the whip such that it is more flexible at the tip to negotiate blood vessels and the like. In FIG. 12, the helical coil whip antenna 306 is tapered on the proximal end 515 to stiffen the flexibility at the distal end 415. In FIG. 13, the helical whip antenna 306 is tapered at both ends. The taper can be adjusted to provide the desired flexibility gradient. The taper can also repeat at regular intervals (either smoothly or at a sudden transition) or coils of different diameters can be placed anywhere within the length of the helical coil whip antenna 306. Alternatively, the distal end 109 of the probe shaft 105 can be tapered to improve the transition between the probe shaft 105 and any type of whip antenna (a helical coil whip antenna 306 is shown) as shown in FIG. 14.

Figure 28:
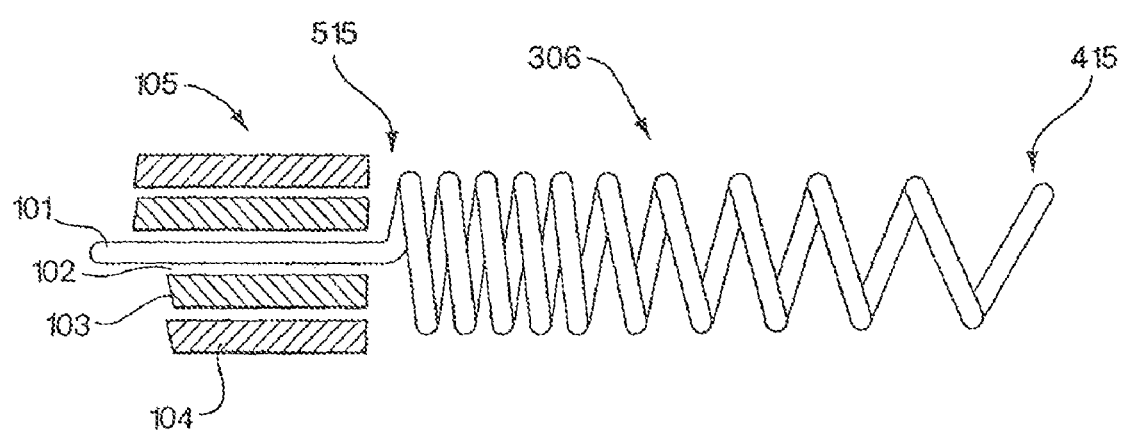
FIG. 28 shows a potential embodiment of a helical whip antenna where the spacing between the coils varies along the length of the helical coil antenna.

In addition to altering the diameter of the coils in the helical coil whip antenna 306, the spacing between the coils can also be modified. As shown in FIG. 28 the spacing of the coils can be closer together at the proximate end 515 and further apart at the distal end 415. This arrangement may allow the construction of a helical coil whip antenna that has greater electrical length but preserves the desired mechanical properties present in a looser packed coil. Alternatively to FIG. 28, the coil spacing could be altered so that the spacing is tighter at the distal end 415 than the proximate end 515, the coil spacing could follow any type of regular change from tighter to looser coils along its length, or the coil spacing could have coils of random spacing.

The modifications to the diameter and spacing of the coils described above are not limited to helical coil whip antennas 306, but could be used with any of the helical coils 208 described above in order to gain mechanical benefits from such a coil design.

In at least some of the variations of the designs, the optimum coil length may be preferably calculated or measured as the length that minimizes the real component of the impedance of the antenna as the impedance of the antenna is measured at the point where the shield ends. This length is usually around 0.25 or less times the electromagnetic wavelength of the RF MRI signal in the medium, but other lengths could be used as would be understood by one of skill in the art.

Figure 15:
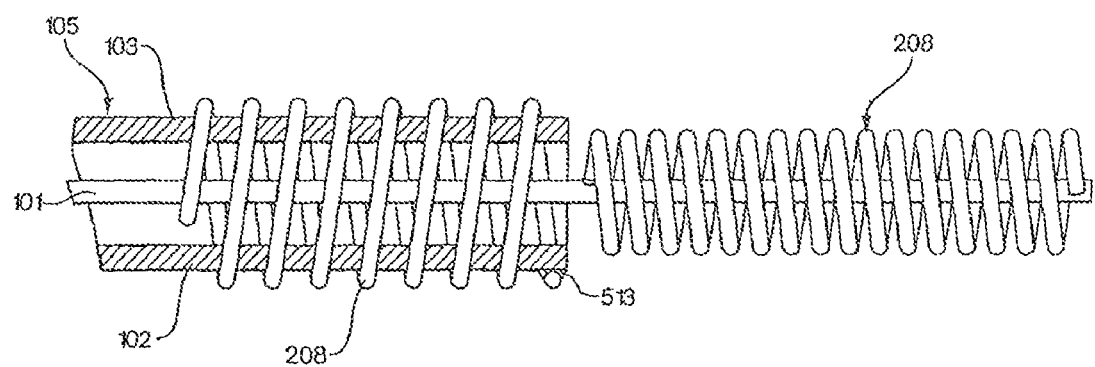
FIG. 15 shows an embodiment in which a second helical coil may be placed around the probe shaft and connected to the shielding.
Figure 16A:
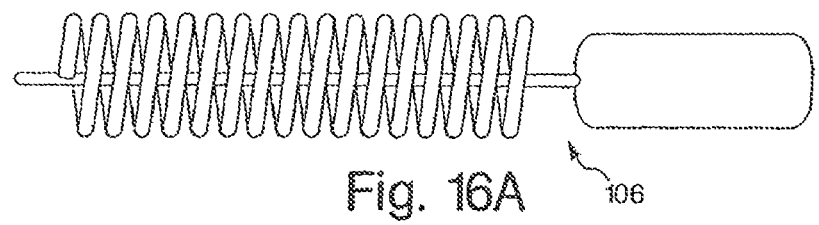
FIG. 16 shows an embodiment in which a second helical coils may be used as shielding around various whip antennas of the disclosed systems, devices, assemblies, probes, and methods.
Figure 16B:
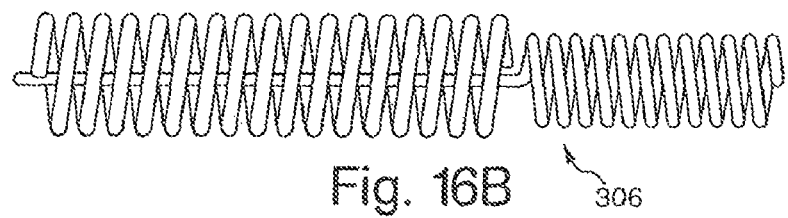
Figure 16C:
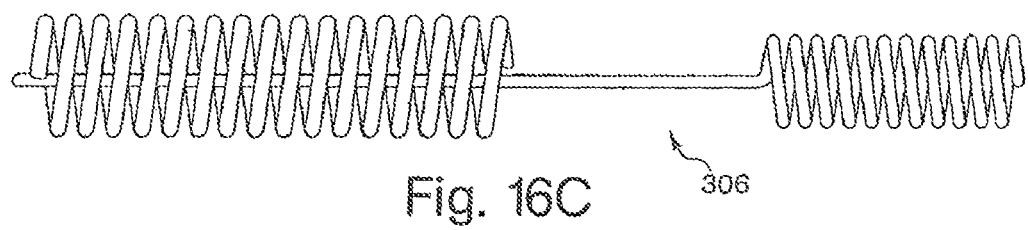
Figure 16D:
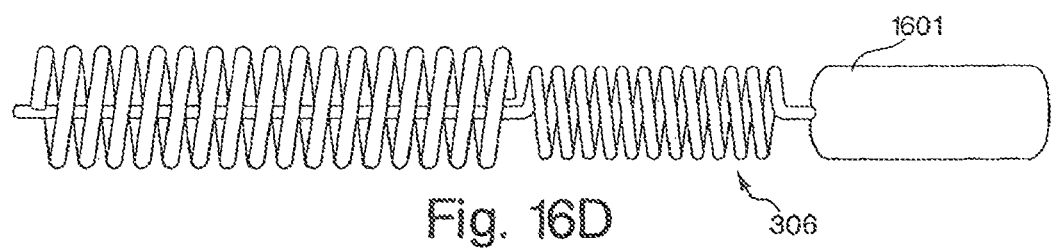

FIG. 15 shows yet another embodiment of the disclosed systems, devices, assemblies, probes, and methods, a second helical coil 408 is connected to the shielding 103 at point 513 of the probe shaft 105 to concentrate the MRI signal sensitivity to a narrow range. The second helical coil 408 can also be connected to multiple points for multiple different electrical properties as would be understood by one of skill in the art. In further alternative embodiments, the shield 103 is completely replaced by the second helical coil 408 which extends for the length of the shaft, insulated from the core 101 by dielectric 102. These arrangements can be used with any type of whip antenna including, but not limited to, those shown in FIG. 16. In particular, a linear whip antenna 106 as shown in FIG. 16A and 16E, a helical coil whip antenna 306 with a separation between the outer shield and whip as shown in FIG. 16B, a helical coil whip antenna 306 without a separation between the outer shield and whip as shown in FIG. 16C or an alternate combination whip with a linear extension 1601 attached to a helical coil whip antenna 306 as shown in FIG. 16D, as well as with any of the other antenna whip designs and herein disclosed or otherwise known to one of skill in the art.

Figure 16E:
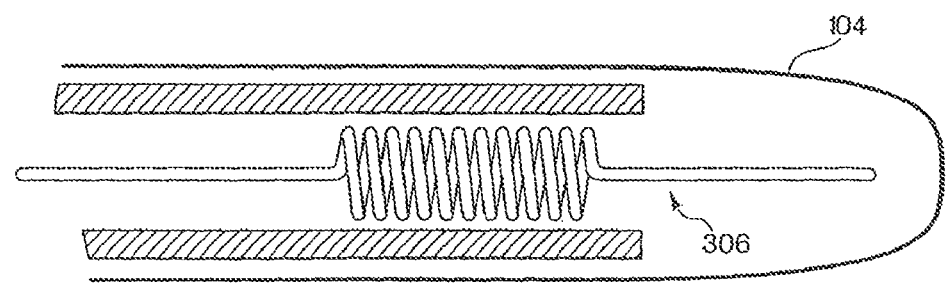

In further embodiments of the disclosed systems, devices, assemblies, probes, and methods the second insulator/dielectric 104 is extended over the second helical coil 408 so as to provide protection to the subject from the antenna's interaction with exposed body fluids, tissues, or other portions of the subject as is depicted in FIG. 16E. The second helical coil 408 can also have any alterations of the coil's diameter or spacing along the second helical coil's 408 length as have been previously discussed with regards to the helical coil whip antenna 306.

The connection between this electronic circuit and the probe is a further portion of the disclosed systems, devices, assemblies, probes, and methods because a standard RF BNC connector as is known to the art is not well suited for frequent connection and disconnection. In many current procedures where an MRI guidewire might be desired, the tools used as part of those procedures must be changeable without having to remove the guidewire from the subject. In one of the embodiments of the present disclosed systems, devices, assemblies, probes, and methods, a connector is used to make an electrical connection between the probe and a tuning/matching and decoupling circuit or interface box of the present disclosed systems, devices, assemblies, probes, and methods. This connector connects the interface to the antenna and can be removed and reinstalled as required during an interventional procedure to load and unload other interventional devices. FIGS. 17 through 25 show some examples of connectors of the disclosed systems, devices, assemblies, probes, and methods which are discussed in detail below.

Figure 26:
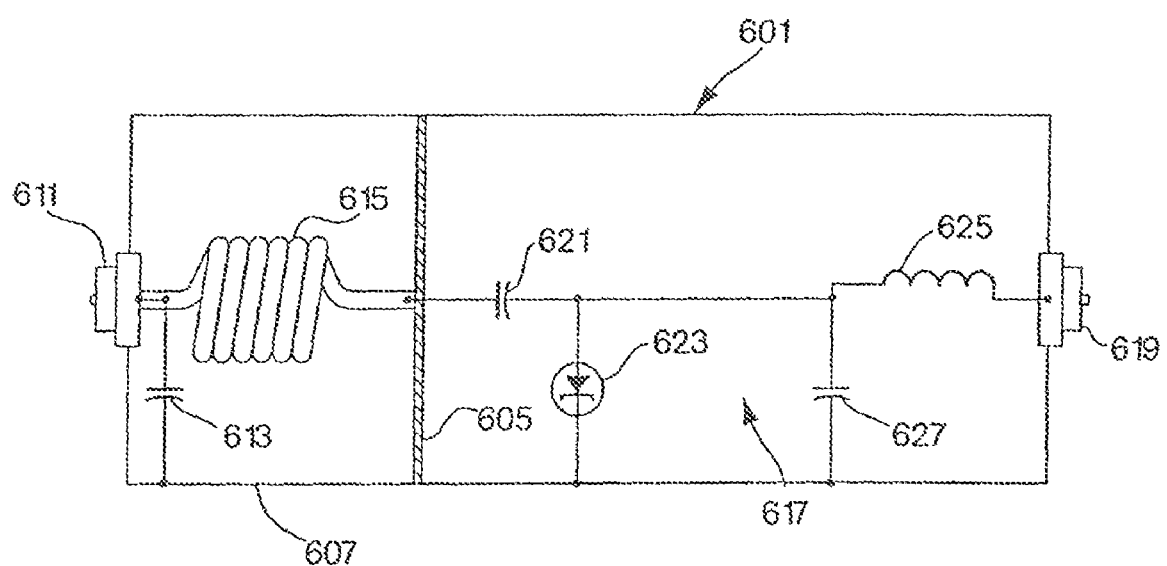
FIG. 26 shows a potential design of an interface box of the instant disclosed systems, devices, assemblies, probes, and methods.

FIG. 26 shows one embodiment of an interface box for use between the MRI machine and the probe or guidewire of the disclosed systems, devices, assemblies, probes, and methods. One embodiment of the interface box has a shielded box 601 with two compartments 607 and 617, separated by a partition 605. In one embodiment, all components are non-magnetic. The probe attaches to coaxial connector 611 or another mating connector portion designed to attach to the connector portion of the probe. Coaxial connector 611 can be insulated from the interface box 601. The balancing of the dipole 611 is accomplished by capacitor 613 and coil 615. Coil 615 in one embodiment is a short length (5-10 cm) of 1 mm diameter solid-shield, 50 ohm coaxial cable, which is wound into a coil, increasing the inductance of both the center conductor as well as the shield. For the balancing function, it can be important to present a high impedance to current flow in the shielding 103 of the probe near the interface box 601. This high impedance is accomplished by tuning the LC circuit formed by capacitor 613 and the inductance of the shield of coil 615. In practice, capacitor 613 is selected such that the impedance of the network having capacitor 613 and coil 615 matches the impedance of the shielding 103 of the probe. The shield portion of the coaxial cable that forms coil 615 can be electrically connected to the partition 605 of the interface box 601 as shown in FIG. 26.

The center conductor of the coaxial cable that forms the coil 615 feeds through the partition 605 in the interface box 601. The inductance of the center conductor of the coil 615, and capacitor 613, form a tuned circuit that can decouple the probe from the imaging pulses of the MRI machine connected at -axial connector 619 (these imaging pulses usually occur at 63.9 MHz). Capacitor 621 can be tuned to maximize probe impedance when PIN diode 623 is turned on during imaging pulses. PIN diode 623 is turned on by a DC level being applied to co-axial connector 619 by the MRI scanner during MRI pulse transmission.

The probe can be tuned to match the generally 50 Ohm impedance of the MRI scanner amplifier by the network of inductor 625 and capacitor 627. This tuning can be accomplished by connecting a network analyzer to coaxial connector 617 and varying the value of the capacitor 627 until the measured impedance is the commonly desired 50 Ohms at 63.9 MHz. These numerical values are given as examples and in no way limit the choice of values that could be chosen in use of the disclosed systems, devices, assemblies, probes, and methods.

The end of the antenna can have a connector portion that allows radio frequency signals to propagate from the scanner to the antenna and vice versa by connecting the connector portion to a mated connector portion. This connector can be a standard BNC connector or one of the special miniaturized connectors shown in FIGS. 17 through 25. The connectors allow for direct insertion of the probe into interventional devices such as balloon angioplasty catheter, stent placement devices. For this to be possible, the connector diameter should be no larger than the probe diameter. Standard connector sizes, however, are often larger than the probe diameter and therefore do not allow for rapid exchanging of interventional devices over the probe. To overcome this difficulty, we show eight different connector configurations. Although many other designs are possible, the most important feature of these designs are that the diameter of the connector portion on the probe is not significantly larger than the diameter of the probe.

The connectors shown in FIGS. 17 through 20, 24, and 25 enable direct electrical contact between the conductors (shield and inner conductor of core) whereas the connectors shown in FIGS. 19-23 have no direct electrical contact.

Figure 17A:
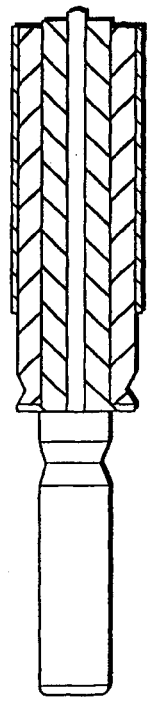
FIG. 17 shows a potential snap-on connector of the instant disclosed systems, devices, assemblies, probes, and methods. 17A shows the male connector portion and 17B shows the female connector portion.
Figure 17B:
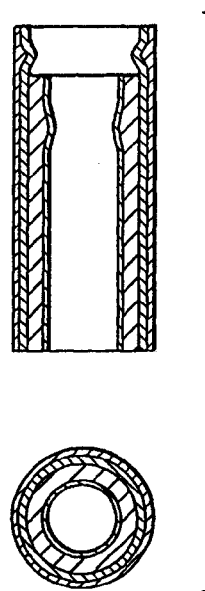

FIG. 17 shows a snap-on connector. The connector at FIG. 17A is the male connector portion. Its diameter is smaller or the same size as the diameter of the guidewire probe. FIG. 17B is the female mated connector portion. They are connected to one other with a small amount of pressure in the direction along the length of the connector and removed easily by pulling the connectors apart.

Figure 18A:
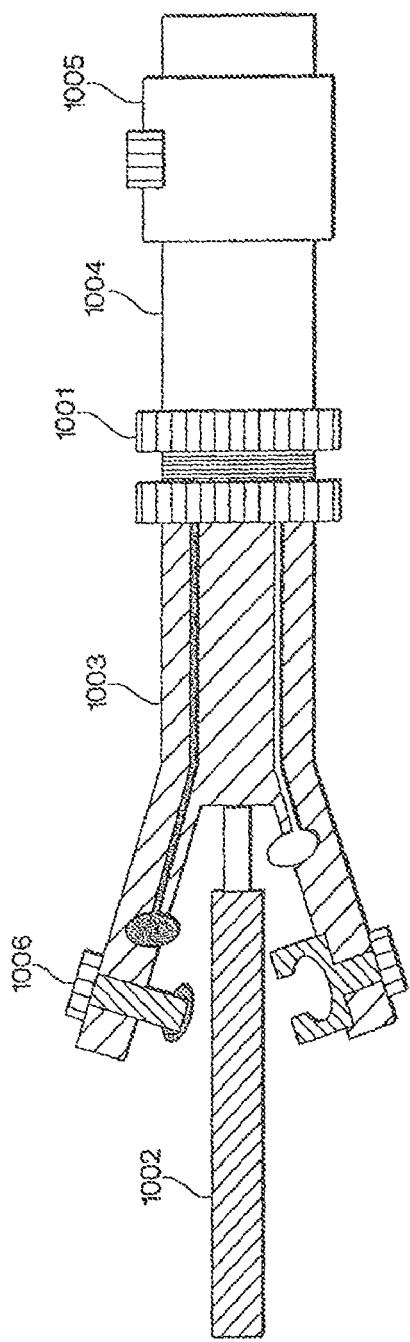
FIG. 18 shows a clip connector of the instant disclosed systems, devices, assemblies, probes, and methods. 18A is in unlocked form and 18B is in locked form.
Figure 18B:
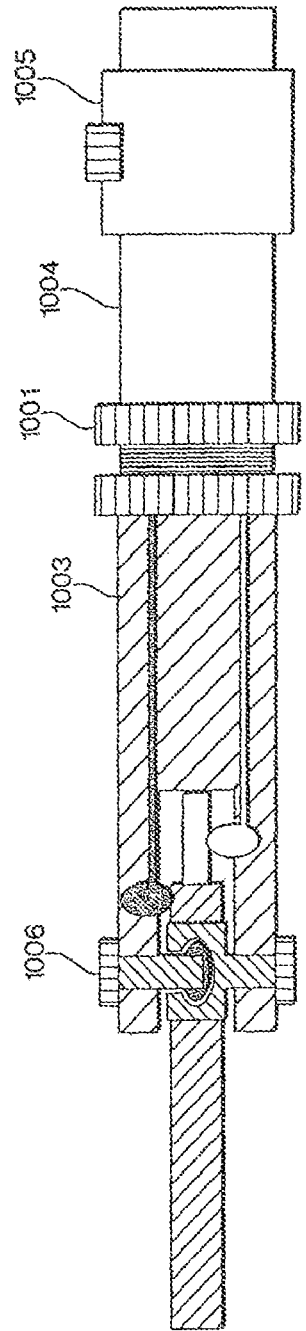
Figure 25:
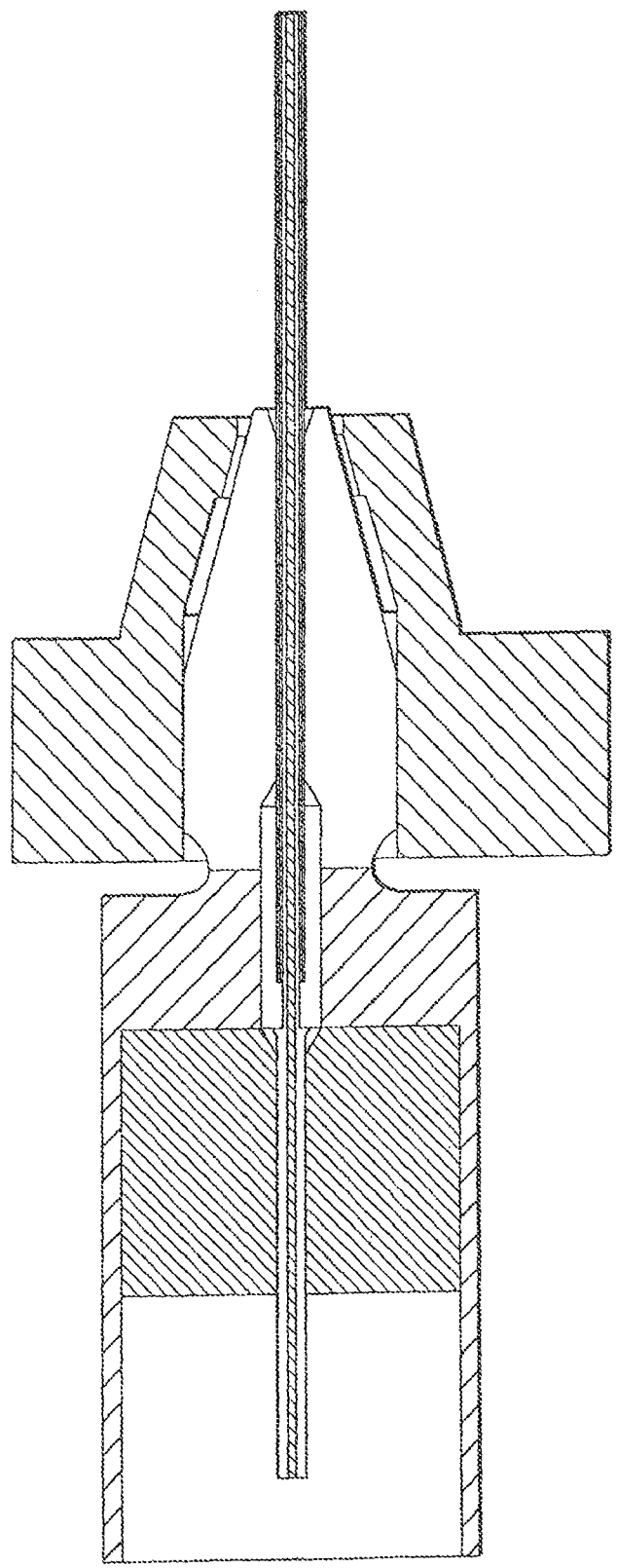

FIG. 18 shows a clip connector. The male connector portion's 1002 diameter is not larger than the diameter of the probe. With a clip lock mechanism, 1006, the female mated connector portion 1003 is connected to the male connector portion 1002. The mechanism shown by FIG. 18 enables free rotation of the connector. This enables the user to freely rotate the probe while it is connected. 1004 shows a coaxial cable connecting the interface box 1005 to the mated connector portion. FIGS. 24 and 25 show an alternative design of this type of connector wherein a vice-like connection is employed instead of the clip. Again this design allows for the probe to rotate freely while it is connected.

Figure 19:
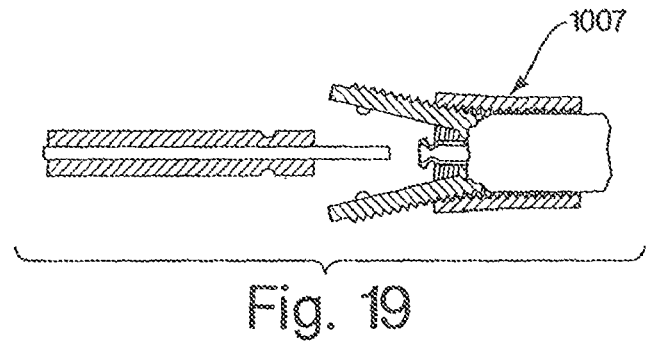
FIG. 19 shows a screw-lock connector of the instant disclosed systems, devices, assemblies, probes, and methods.

FIG. 19 has the screw 1007 on the female mated connector portion that is an alternative to the clip lock mechanism, 1006 shown in FIG. 18.

Figure 20A:
FIG. 20 shows a screw style connector of the instant disclosed systems, devices, assemblies, probes, and methods. 20A shows the female portion and 20B shows the male portion.
Figure 20B:

FIG. 20 shows another type of screw connector. FIG. 20A is the female connector portion that is a part of the guidewire probe. The male mated connector portion shown in FIG. 20B can be connected to a coaxial cable that leads to the interface box.

One problem with the connectors shown in FIGS. 17 through 20 is difficulty in using in a wet environment. When the connectors are wet or have blood or other body fluids on them, their performance may degrade. Therefore, a connector was designed that can be used in wet environment. The connectors shown in FIGS. 21-23 do not require direct electrical contact between the two connector portions.

Figure 21:
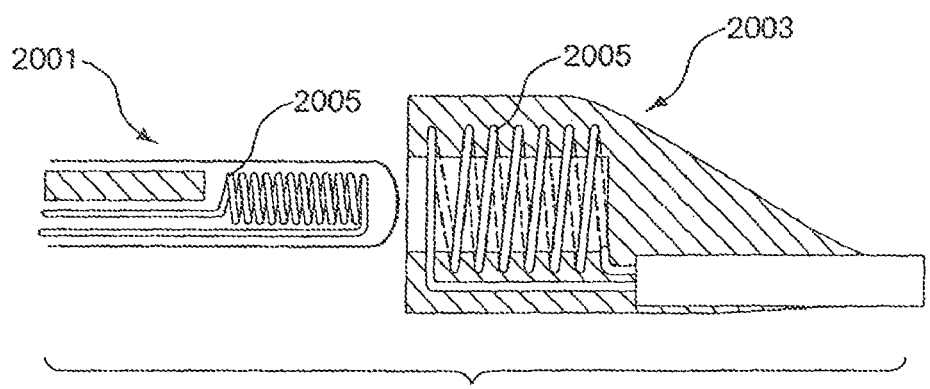
FIGS. 21-23 show alternate connectors whereby there is no direct electric contact between the male and female members of the connector.

FIG. 21 shows a solenoidal coil 2005 inside both female and male connectors portions. The male connector portion snaps in the female mated connector portion 2003 but the electrical wires are not touching one other. The signal is transmitted from one to the other by electromagnetic waves.

Figure 22:
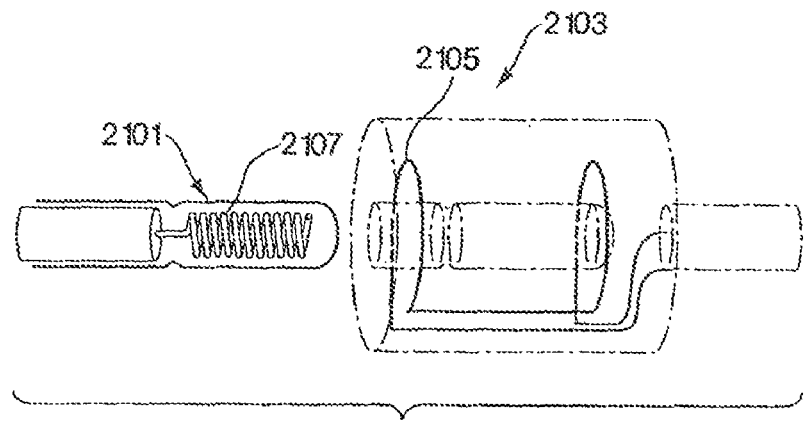

FIG. 22 shows a coaxial cable with extended inner conductor 2105 as the mated connector portion 2103 and an opposed solenoidal coil 2107 as the connector portion 2101 on the guidewire probe.

Figure 23:
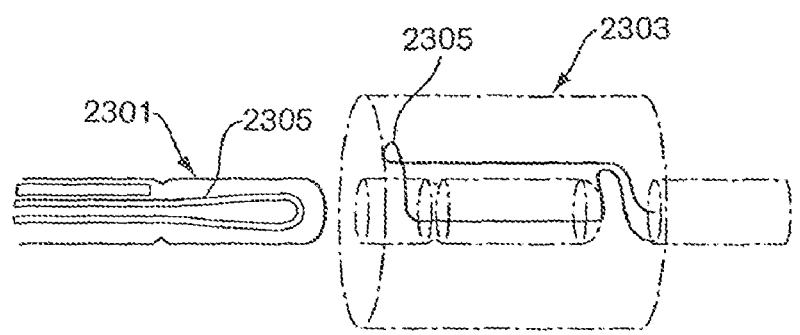

FIG. 23 shows a loop coil 2305 in both ends of the connector. As in the other, the male connector portion 2301 snaps on the female mated connector portion 2303. The electromagnetic waves are transmitted from one coil to the other enabling connection.

One further advantage of using these connectors (FIGS. 21-23) are the isolation of the circuits. Any direct current from one connector should typically not appear on the other.

Figure 27:
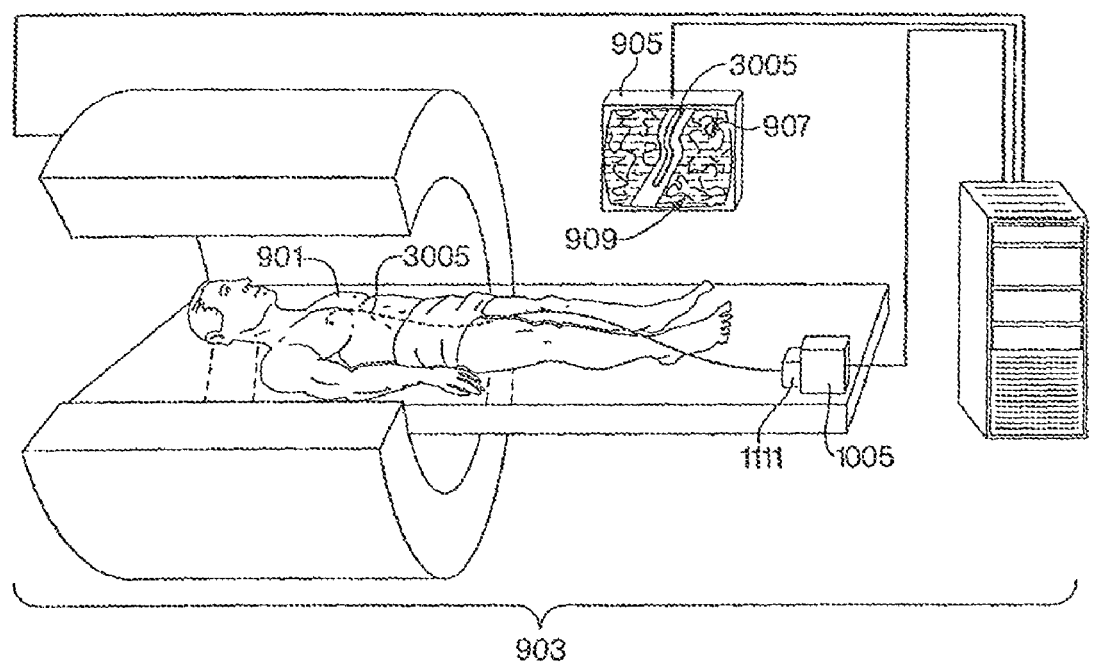
FIG. 27 shows a layout of a system of the instant disclosed systems, devices, assemblies, probes, and methods wherein the guidewire probe might be used.

FIG. 27 shows one potential layout of a system whereby a probe could be used. In this figure, the subject 901 is shown within the MRI machine 903. The probe 3005 has been inserted into the subject 901. The monitor 905 shows an MRI 907 including the probe 3005 and the surrounding biological tissue 909. The probe 105 is connected to the interface box 1005 through a connector 1111 that allows an operator to load or unload tools without removing the probe 3005 from the subject 901. The interface box 1005 is connected to the MRI machine 903 allowing the MRI machine 903 to use the probe 3005 as an active antenna in the subject 901.

Figure 29:
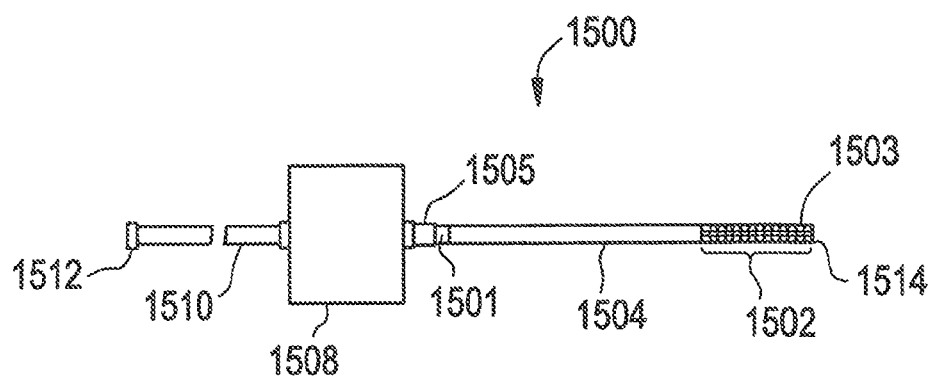
FIG. 29 shows a schematic diagram of an imaging probe system.

FIG. 29 shows an embodiment of an imaging probe system 1500 that may be configured for use in the vascular system.

The imaging probe system 1500 can be dimensionally adapted for intravascular use, with an outer diameter in one embodiment in the range of 0.025-0.035", for example. 0.032", and with an outer diameter in another embodiment of in the range of 0.014-0.018", for example, 0.014". The probe may also be dimensionally adapted for insertion into other anatomical features. For example, a probe for esophageal insertion could have an outer diameter in the range of about 3 to about 30 French, preferably about 9 French. A probe for transrectal insertion can have an outer diameter in the range of about 0.5 French to about 60 French, preferably about 15 French. A probe for prostate imaging can have an outer diameter in the range of about 0.5 to about 10 French, preferably about 10 French. A probe for transvaginal insertion can have an outer diameter in the range from about 0.5 to about 60 French, preferably about 9 to 14 French. A probe for gastrointestinal insertion can have an outer diameter in the range from about 1 French to about 20 French, preferably about 15 to 17 French. A probe for transurethral insertion can have an outer diameter of about 6 to 17 French, preferably about 13 French. A probe for fallopian tube insertion can have an outer diameter in the range from about 1 French to about 6 French, preferably about 1 to 3 French.

In certain embodiments, the imaging probe system 1500 may be introduced into the body of a subject directly into the vascular system, through, for example, the femoral artery or vein using a standard introducer. The imaging probe system 1500 may then be advanced through the vascular system to the region of interest either under fluoroscopic or MR guidance. The imaging probe 1500 has a proximal end 1501 attachable to an interface box 1508, which in turn is attachable to an MRI machine (not shown). The imaging probe 1500 further has a distal end 1503 suitable for advancing through the vascular system of a subject.

As depicted in FIG. 29, an imaging probe 1500 for intravascular use may include an imaging coil 1502 in electrical communication proximally with a modified coaxial cable 1504. The modified coaxial cable 1504 in electrical communication with the imaging coil 1502 has a loopless antenna. In the depicted embodiment, the imaging coil 1502 and the insulating shielding of the coaxial cable 1504 form a closed RF circuit, and RF signals generated by the hydrogen protons in the water molecule during MR scanning are collected by the imaging coil 1502 and then transmitted to the MR scanner through the coaxial cable 1504 and interface box 1508, as will be described in more detail below.

As depicted in this and subsequent figures, the coaxial cable 1504 may include a conductor core sandwiched concentrically in layers of insulation/dielectric, conductive shielding and dielectric/insulation respectively. The construction of the imaging probe 1500 may include a simple coaxial cable 1504 with its top layers of insulation and shielding removed in certain sections, as will be described in more detail below. In those sections where the top layers of insulation and shielding have been removed, the central conductor of the coaxial cable 1504 can be exposed. The exposed central conductor may then be attached to the imaging coil 1502 to maintain electrical communication therewith. In certain embodiments, the imaging coil 1502 may be made from a wire wound on a mandrel, for example a gold-platinum-iridium winding wire.

As shown in FIG. 29, and as described in more detail below, the imaging coil 1502 is disposed distally on the imaging probe 1500. The imaging coil 1502 serves to gather the RF signal. In one embodiment, the imaging coil 1502 includes a specific length of gold-platinum-iridium wire wound into a spring with a prescribed pitch. In an embodiment, the wire can be a wound wire. The wound wire can have a diameter of about 0.003 inches. In an embodiment, the pitch of the winding can be in the range of about 0.004 inches to about 0.015 inches. In an embodiment, the pitch can be about 0.012 inches. As will be described below, the imaging coil 1502 can be positioned over, covering, or surrounding the insulated conductor core of the coaxial cable 1504. More specifically, the conductor core may be made from a Nitinol wire plated with gold-silver-gold and then covered with a thin insulating layer of polymeric FEP. The polymeric layer insures complete electrical insulation between the core and the imaging coil 1502 except at the proximal end of the imaging coil 1502 where it has been attached to the core in electrical communication therewith.

In one embodiment, the imaging coil 1502 length is about 0.25 times the wavelength in the medium, which is a complex function of various parameters such as the dielectric constant of the insulator, the thickness of the primary insulator, the frequency, and the electrical properties of the environment around the antenna. The length of the imaging coil 1502 which acts as an RF antenna can be straight but is coiled in this case. The coil shape may help intensify the signal near the imaging coil 1502. The coil shape can be straight, ground, wound, braided, multiple pitches, combinations of these, and other shapes known in the art. The imaging coil can include a solid object, such as a core or a hypotube. There need not be insulation between the imaging coil and the corewire. A plastic could be extruded over the imaging coil. A lubricious coating could be applied to the plastic.

The coaxial cable 1504, described below in more detail, connects the proximal end 1501 of the imaging probe 1500 to an interface box 1508. At the proximal end of the coaxial cable 1504 is a connector such as a Suhner MMCX connector. The interface box 1508 in turn connects the probe 1500 to the MRI scanner (not shown). An extension cable 1510 with a connector such as a BNC connector 1512 may provide the connection between the interface box 1508 and its contained circuits and the MRI scanner (not shown). The circuitry housed in the interface box 1508 is described below in more detail.

As shown in FIG. 29, a flexible tip 1514 is attached at the distal end of the imaging probe system 1500 distal to the imaging coil 1502. The flexible tip 1514 may have a spring. The flexible tip 1514 may be attached to the distal end of the coaxial cable 1504. The flexible tip 1514 will be described in more detail below.

Figure 30:
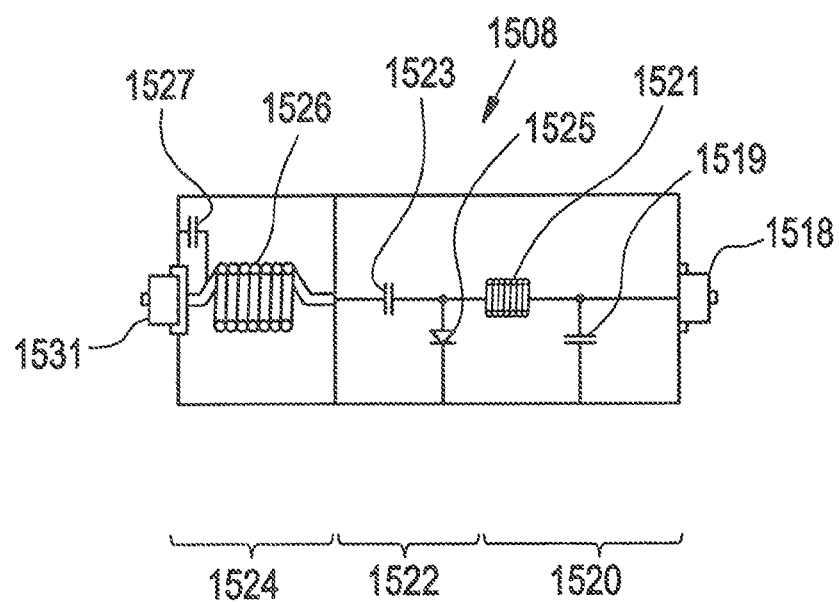
FIG. 30 shows a schematic diagram of the circuitry within the interface box.

FIG. 30 provides a diagram of the circuitry within the interface box 1508. Providing attachment between the interface box 1508 and the proximal end of the coaxial cable (not shown) may be a BNC connector 1518. In electrical communication with the imaging probe (not shown) are three circuits, a tuning-matching circuit 1520, a decoupling circuit 1522 and a balun circuit 1524. The imaging probe (not shown) may be connected to the interface box 1508, and the interface box 1508 may further be connected to the appropriate coil port of the MRI scanner using a 50-200 cm long RGO58 coaxial cable with BNC connectors. A ground isolated Micro BNC (MMCX) connector 1531 or any other suitable connector provides electrical communication between the circuits in the interface box 1508 and the coaxial cable (not shown) attaching the interface box circuits to the MRI machine (not shown). With such a long cable (e.g., 50-200 cm) it is desirable to maintain constant impedance and to avoid loops within the MRI. A cable accessory to perform these functions may be added to the system described herein, as will be familiar to practitioners of ordinary skill in the art.

Circuits in the interface box 1508 perform three functions. First, the tuning-matching circuit 1520 matches the impedance of the antenna/cable to the input of the scanner to optimize performance. Second, the decoupling circuit 1522 detunes the imaging probe during scanner coil transmit, using DC current supplied through the scanner connection to prevent heating. Third, the balun circuit 1524 prevents excess currents from being induced in the scanner. The arrangement of the circuits within the interface box 1508 represent an exemplary embodiment thereof. It will be understood by those of ordinary skill that some modifications in interface circuitry may be required for different commercially available MR scanner models.

The underlying principle of operation for the decoupling circuit 1522 may be explained as follows: the MRI signals are excited in the patient's tissue by the MRI scanner's transmitter coil; this transmission may induce a current in the imaging probe during excitation, which could result in the production of heat. The decoupling circuit 1522 allows this induced current to be shorted out. The decoupling circuit 1522 includes a capacitor 1523 and a diode 1525. The diode 1525 in the decoupling circuit 1522 is activated by a standard low voltage signal provided by the scanner during MR transmission. The DC current generated by the scanner activates the diode 1525 which in turn grounds the DC current, preventing the imaging probe from being exposed to the full current and thus reduces heating. However, for normal AC signal currents in the receiving phase, the diode 1525 is not active and the circuit functions normally.

The tuning-matching circuit 1520 includes a capacitor 1519 and an inductor 1521 in parallel to match the impedance of the entire circuit to 50 ohms, the input impedance required by the preamplifier of the scanner. The balun circuit 1524 has a rigid coaxial cable inductor coil 1526 and a capacitor 1527 connecting the ground to the case of the interface box 1508. The values of the capacitors described above and the inductor 1521 may be determined on a network analyzer for the completed imaging probe system at the time of manufacture.

Figure 30A:
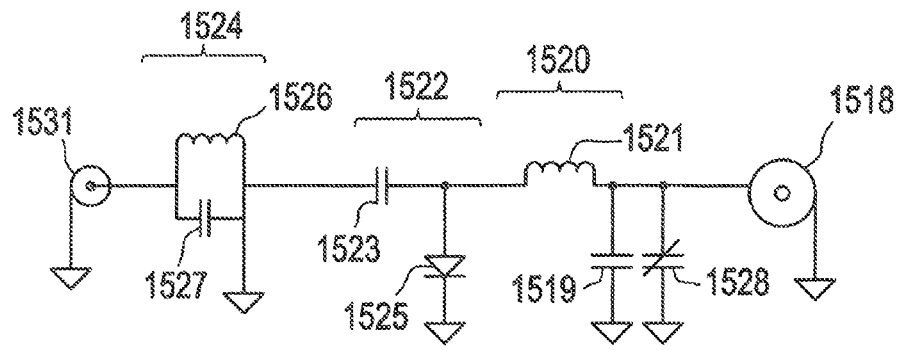
FIG. 30A shows a schematic diagram of the circuitry within the interface box.

FIG. 30A shows a another schematic diagram of an exemplary embodiment of an interface 1508'. It may include a balun circuit 1524 having a capacitor 1527 and an inductor 1526, a decoupling circuit 1522, having a capacitor 1523 and a diode 1525, and a tuning/matching circuit 1520, having a capacitor 1519 and an inductor 1521. Capacitor 1527 may be a porcelain capacitor and may have a capacitance of about 39 picoFarads (pF). Inductor 1521 may be a tunable inductor and may have an inductance of about 198 nanoHenrys (nH). Capacitor 1523 may be a porcelain capacitor and may have a capacitance of about 100 pF. Diode 1525 may be a PIN diode. Capacitor 1519 may have a capacitance of about 22 pF. The interface 1508' may further include a proximal connector 1531 and a distal connector 1518, as described above. The interface may further include a variable capacitor 1528. The variable capacitor 1528 facilitates fine adjustment of the tuning/matching circuit 1520. The variable capacitor 1528 may be a ceramic capacitor and may be variable in the range of about 5.5 pF to about 30 pF.

FIGS. 34A-E depicts various views of an exemplary embodiment of an interface box 3400. FIG. 34A shows a perspective view of the interface box 3400. FIG. 34B shows a side view. In this exemplary embodiment, the proximal connector 1531 emerges from one side of the interface box 3400, and the distal connector 1518 emerges from an opposing side.

FIG. 34C depicts a top cross sectional side view of the interface box 3400. The inner surface 3402 of the box 3400 may have a shield coating. The shield coating can effect a −50 dB shielding at a predetermined frequency, such as 63.86

MHz. The box 3400 may have a proximal aperture 3406 for the proximal connector (not shown) and a distal aperture 3404 for the distal connector (not shown). The shield coating may be applied up to the edge of one or both apertures 3404, 3406, or can be masked in areas surrounding one or both apertures 3404, 3406.

FIG. 34D depicts a side cross sectional view through cut line B of FIG. 34C. Aperture 3404 is positioned on a side of box 3400. The box 3400 may have a lid section 3410 and a base section 3408.

FIG. 34E depicts a side cross-sectional view through cut line A of FIG. 34C. Aperture 3406 is positioned on a side of box 3400.

Figure 31:
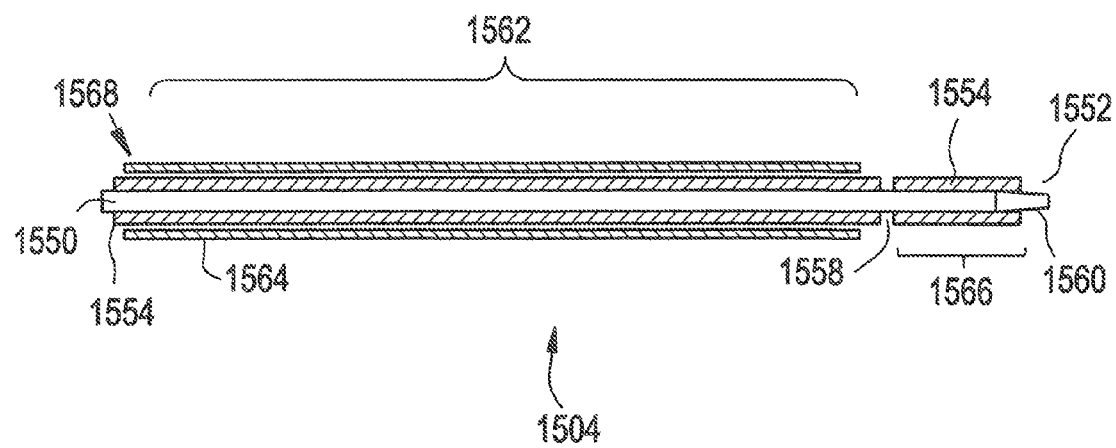
FIG. 31 shows the layers of the coaxial cable assembly.

FIG. 31 shows in more detail a coaxial cable assembly 1504 included in the previously-described imaging probe system. The coaxial cable 1504 and its relation to the imaging probe system will also be described in more detail below. In one embodiment, the coaxial cable 1504 has a core 1550 made of a non-ferromagnetic conductive material, for example, Nitinol plated with precious metal. The plating may provide multiple layers of different metals, for example gold-silver-gold. Other materials for the core 1550 with appropriate properties may readily be envisioned by practitioners of ordinary skill. In one embodiment, the core 1550 may have a diameter in the range of up to about 0.014 inches, preferably 0.0085 inches and may be taper ground at its distal tip 1552. Alternate configurations of the distal tip 1552 may also be provided, for example, barrel grinding or plunge grinding.

A primary insulation layer 1554 covers the core 1550 except where the primary insulation layer 1554 has been removed to expose the underlying core 1550. The primary insulation layer 1554 may use a plastic material such as FEP or another suitable insulator. As shown in this figure, a first and a second bare area, 1558 and 1560 respectively, are shown where the primary insulation layer 1554 is absent. The primary insulation layer 1554 can be removed to create either or both bare areas. Removal may be accomplished by using a razor blade or a similar or similarly functioning tool. The bare areas may also be created by not applying insulation in the regions of the bare areas or by applying insulation discontinuously along the core. Between the first bare area 1558 and the second bare area 1560 is disposed a distal coaxial cable segment 1566 where the primary insulation 1554 covers the core 1550. Surrounding this distal coaxial cable segment 1566 is the imaging coil (not shown) in the complete imaging probe system. The first bare area 1558 is also termed the joining segment.

Covering the primary insulation layer 1554 over the proximal shaft 1562 of the coaxial cable 1504 is a coaxial shield layer 1564. This coaxial shield layer 1564 may be made of Nitinol or another suitable material. In one embodiment, a Nitinol hypotube is used with a diameter of 0.010-0.035" for an imaging probe with a substantially similar diameter. Additional layers may cover the coaxial shield layer 1564. For example, gold or other precious metal plating may cover the coaxial shield layer 1564 along some or all of the proximal shaft 1562. In an embodiment, approximately 2 cm of the proximal end 1568 of the coaxial shield layer 1564 may be goldplated, or gold plating may be extended more distally along the coaxial shield layer 1564, as will be appreciated by practitioners of ordinary skill in the art, for the purpose, for example, of increasing conductivity of the loopless antenna. Goldplating can facilitate attachment of a connector.

FIG. 32 depicts in more detail an embodiment of an imaging probe 1500 that can be adapted for intravascular and other uses. The proximal shaft 1562 includes a coaxial cable 1504, for example a coaxial cable described with reference to FIG. 31. As depicted in FIG. 32, the proximal shaft may also include an extended flexible shield or proximal spring assembly 1580. In one embodiment, to optimize the mechanical characteristics along the distal end of the coaxial shield layer 1564, the Nitinol hypotubing of the coaxial shield layer 1564 may be heat treated to increase its flexibility and a MP35N spring may be soldered to the distal end of the coaxial shield layer 1564 to form the proximal spring assembly 1580. The proximal spring assembly 1580 may be joined to the coaxial shield layer 1564 by a conductive epoxy, laserweld or solder joint, as will be understood by those of ordinary skill in the art. The proximal spring assembly 1580 may combine with the coaxial shield layer 1564 to act as a contiguous coaxial shield while providing optimal mechanical characteristics in that region. The combination of the heat treated hypotube and the MP35N spring acts as a strain relief to improve the transition from the hypotube to the inner core. In this arrangement, there is no significant loss to the electrical properties with this improved transition. The proximal spring assembly 1580 may be fabricated from a variety of materials, in one embodiment using Tantalum or MP35N, for example using a 0.003 in. round winding wire that may be stacked. While the aforesaid materials have been chosen primarily for their MR compatibility and conductance while providing desirable mechanical properties such as column strength and kink resistance, other materials and arrangements thereof may be selected to serve the same function. As shown in this figure, the proximal spring assembly 1580 may replace distally the coaxial shield layer 1564 that is fabricated from, for example, a Nitinol hypotube. Alternatively, the proximal spring assembly 1580 may be omitted, so that the coaxial shield layer 1564 continues uninterrupted along the entire length of the proximal shaft 1562.

In the fabrication of this embodiment, the primary insulator 1554 may be attached to the core 1550, for example, a gold-silver-gold plated Nitinol wire. This can be done by means of extrusion, drawing, a heat shrink tubing, or another method known to the art. Next, the conductive shielding 1564 may be loaded on the core-insulator assembly in the proximal sections. This can be done by means of braiding, plating, painting, depositing, sputtering, etc. Alternatively, a metallic hypotube fabricated from a material like Nitinol can be used instead of braiding to add mechanical stiffness. The Nitinol hypotube may be heat-treated over an area at its distal end or modified in other ways familiar to artisans for increasing flexibility of the hypotube as it approaches the transition area with the spring. An outer insulating layer 1584 may be used to cover the entire assembly.

FIG. 32 further shows the imaging coil 1502 coiled around the distal coaxial cable segment 1566 (shown in FIG. 31). The imaging coil 1502 is an electrical communication with the core 1550 at the first bare area 1558 by virtue of a solder junction 1582. Dimensions of the imaging coil 1502 may also be modified, so that the length may range up to 12 centimeters and the pitch may be increased up to about twice the current one. In an embodiment, the imaging coil can have a length of about 6 inches. Pitch may be selected in association with selection of length dimension so as to obtain a total length for the imaging coil of about $\frac{1}{4}\lambda$, a length desirable for minimizing noise resistance and heating, where $\lambda$ is the wavelength of the magnetic resonance signal when the imaging probe is in vivo or in a sample. Various materials suitable for the imaging coil 1502 may also be substituted, for example copper instead of platinum. An insulating coating layer 1584 extends along the proximal shaft 1562 of the imaging probe 1500 and may extend distally to cover the imaging coil 1502 until it encounters an adhesive seal (not shown in this figure), depicted in FIG. 33. Distal to the adhesive seal (not shown), an adhesive joint 1588 may attach the spring tip 1514 to the core 1550 and to the primary insulation layer 1554. The spring tip 1514 is affixed distal to the imaging coil 1502 as described in more detail below at an adhesive joint made, for example, from epoxy. Proximal to the coaxial cable 1504, a BNC connector 1512 or another suitable coaxial connector provides electrical connection between the imaging probe system 1500 and the interface box (not shown) and further provides electrical connection between the core 1550 and the coaxial shield layer 1564 at the proximal end 1501.

External to the coaxial shield layer 1564 may be a coating of cover layer 1584, made, for example, from silicone or polyethylene terephthalate (PET), to protect the underlying materials from contact with body fluids. Additionally, a lubricious coating may be provided overlying the coating layer 1584. The coating layer 1584 may extend along a preselected length of the imaging probe 1500, for example, from the adhesive junction 1588 to a proximal portion of the proximal shaft 1564 at a specified distance from the connector 1512.

Figure 32A:
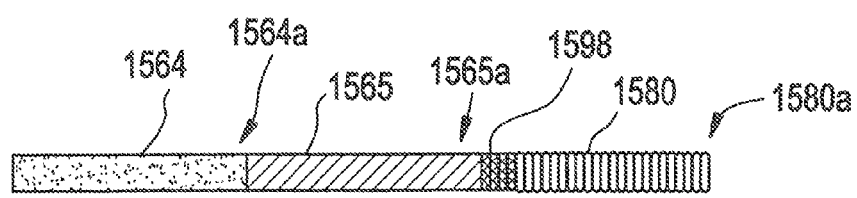
FIG. 32A shows detail of an embodiment of the shield layer.

FIG. 32A depicts an embodiment of a probe having a shield layer 1564 with a distal end 1564a, a modified shield layer 1565 with a distal end 1565a and attached to the distal end 1564a of the shield layer 1564, and a joint 1598 connecting the distal end 1565a of the modified shield layer 1565 to the proximal spring assembly 1580. The joint 1598 may be a conductive joint. The distal end 1580a of the proximal spring assembly 1580 may be joined to an imaging coil (not shown) by an adhesion point (not shown). The adhesion point may electrically insulate the proximal spring assembly 1580 from the imaging coil.

The modified shield layer 1565 may be, e.g., a heat-treated Nitinol hypotube. The modified shield layer 1565 may provide a region of stiffness transition, so that the change in stiffness between the region of the shield layer 1564 and the region of the coil or the spring tip is gradual. Other compositions of the modified shield layer are discussed above.

In the regions where the shield layer 1564 transitions to the modified shield layer 1565 and where the modified shield layer 1565 transitions to the proximal spring assembly 1580, the thickness of the core (1550 in FIG. 32) may be stepped up to help lessen potentially abrupt changes in stiffness. In an embodiment, the shield layer 1564 may include a series of telescoped layers (not shown), progressively decreasing in diameter distally. Such an arrangement can lessen abrupt changes in stiffness.

FIG. 33 depicts in more detail a spring tip assembly 1600 affixed to the imaging probe 1500 at the latter's distal end 1503. The spring tip assembly 1600 may provide flexibility at the distalmost end of the imaging probe 1500 so that the probe may advance more readily through tortuous regions of the vascular anatomy. Not to be bound by theory, the spring tip assembly 1600 may also have an effect on breaking up standing waves to decrease heating. As depicted herein, the spring tip assembly 1600 includes a spring tip 1514 that is affixed to the distal end 1503 of the imaging probe 1500. In one embodiment, the spring tip 1514 may be affixed proximally by means of an adhesive joint 1588 made from an electrically isolating material such as epoxy that prevents electrical conduction between the spring tip 1514 and the imaging coil 1502 or the core 1550 while attaching the spring tip 1514 to the core 1550, the imaging coil 1502, the shield layer 1564, or the insulating layer 1584. The adhesive joint 1588 may further attach a ribbon 1602 to both the core 1550 and to the spring tip 1514.

The ribbon 1602 may extend distally through the coils of the spring tip 1514. In one embodiment, the ribbon 1602 is flat and is made of MP35N. A distal joint 1604, for example a solder-braze joint, affixes the spring tip 1514 to the ribbon 1602-distally and further seals the end of the spring tip 1514. In one embodiment, the spring tip 1514 may be made from a gold-platinum-iridium winding wire 0.003 inches in diameter wound stacked except at joints 1558 and 1602. A layer of outer coating 1584 may cover the spring tip assembly 1600. An epoxy adhesive 1608 seals the imaging coil 1502, the core 1550 and the coating layer 1584. As previously described, a solder junction 1582 attaches the imaging coil 1502 to the core 1550 and provides electrical communication between the two. As previously described, the primary insulation 1564 covers the core 1550 and isolates it from the imaging coil 1502.

In certain embodiments, the spring tip 1514 may be made from approximately 0.003 inch round winding wire stacked. Materials such as tantalum may be used or alloys such as a gold-platinum, MP35N or L605. Stiffness of the spring may be varied by changing materials and altering the arrangement of materials with treatments such as heat treatment, with changing the geometric shapes, with setting up telescoping tubes, and with other similar arrangements. The distal spring assembly 1600 may be attached with conductive epoxy or adhesives, ultrasonic welding, mechanical attachment, soldering or laser welding. In other embodiments, gadolinium may be used in the coating of the guidewire, either with silicone or with a hydrophilic substance, permitting better magnetic resonance tracking of the wire. Other features may be added to improve the operational characteristics of the spring and imaging coil assembly. The imaging probe may include other features such as an extended flexible spring shielding, a longer overall length, a detachable connector with an extendable back end for balloon or guide exchanges, or a connector permitting distal spring change, as will be apparent to those of ordinary skill in the art. The distal spring area could have a flatdropped isolated core or ribbon to provide a stiffness transition top the tip.

While the disclosed systems, devices, assemblies, probes, and methods have been described in connection with the preferred embodiments shown and described in detail, various modifications and improvements thereon will become readily apparent to those skilled in the art. Accordingly, the spirit and scope of the present disclosure is limited only by the following claims.

We claim:

1. A magnetic resonance imaging probe, comprising:
   a probe shaft having a magnetic resonance antenna, the probe shaft comprising
   a core of non-magnetic material;
   a first insulator/dielectric covering the core;
   a shield layer covering the first insulator/dielectric;
   a proximal spring assembly coupled to a distal end of the shield layer and configured and arranged to act with the shield layer as a coaxial shield; and
   a magnetic resonance imaging coil conductively attached to the core and forming a part of the magnetic resonance antenna;
   a spring tip having increased flexibility relative to the probe shaft proximate the antenna; and
   an electrically insulating material affixing the spring tip to a distal end of the probe shaft and preventing electrical conduction between the spring tip and the imaging coil.

2. The probe of claim 1, wherein the core comprises a Nitinol wire and alternating layers of gold, silver, and gold, surrounding at least a portion of the Nitinol wire.

3. The probe of claim 1, wherein the probe shaft further comprises a second insulator/dielectric disposed over the shield layer.

4. The probe of claim 1, wherein the core of non-magnetic material is plated with alternating layers of gold and silver.

5. The probe of claim 1, wherein the core comprises a central core having at least one of carbon, glass fiber, and a polymer, and the core further comprises a radio frequency conductive covering surrounding the central core.

6. The probe of claim 5, wherein the covering comprises alternating layers of gold, silver, and gold, surrounding the central core.

7. The probe of claim 1, wherein the spring tip is attached to the imaging coil by an adhesive joint.

8. The probe of claim 1, wherein the imaging coil comprises a helical whip with a proximate end and a distal end, the helical whip having coils with a diameter and a spacing, and wherein the distal end of the helical whip is connected to the spring tip.

9. The probe of claim 8, wherein the helical whip is covered by a biocompatible material or covering.

10. The probe of claim 9, wherein an electrical length of the imaging coil is chosen so as to compensate for the biocompatible material or covering.

11. The probe of claim 1, wherein the probe is sized and shaped to be a guidewire.

12. The probe of claim 1, further comprising a connector coupled to a proximal end of the probe shaft.

13. The probe of claim 12, wherein the connector is removably coupled to the proximal end of the probe shaft.

14. The probe of claim 12, wherein the connector couples to an interface.

15. The probe of claim 14, wherein the interface comprises at least one of a tuning-matching circuit, a balun circuit, a decoupling circuit, or a variable capacitor.

16. The probe of claim 1, wherein the antenna comprises a loopless antenna.

17. The probe of claim 1, wherein the spring tip further comprises a ribbon extending from the spring tip to the core.

18. The probe of claim 1, wherein an outer surface of the probe shaft is insulated with a biocompatible material or coating.

19. The probe of claim 1, further comprising a cover layer covering at least a portion of the probe shaft.

20. The probe of claim 1, wherein the probe is sized and shaped for intravascular use.

21. A magnetic resonance imaging probe, comprising:
a core of non-magnetic material;
a shield layer having a distal end and surrounding at least a part of the core;
a proximal spring assembly having a distal end and being conductively coupled to the distal end of the shield layer and configured and arranged to act with the shield layer as a coaxial shield;
a joining segment attached to the distal end of the proximal spring assembly;
a magnetic resonance imaging coil attached to the joining segment; and
a spring tip attached to a distal end of the imaging coil.

22. The imaging probe of claim 21, wherein the proximal spring assembly comprises a round winding wire.

23. The imaging probe of claim 22, wherein the round winding wire is stacked.

24. A magnetic resonance imaging probe, comprising:
a core of non-magnetic material;
a first insulator/dielectric surrounding at least a part of the core;
a shield layer surrounding at least a part of the first insulator/dielectric and having a distal end;
a modified shield layer attached to the distal end of the shield layer and having a distal end;
a proximal spring assembly conductively coupled to the distal end of the modified shield layer and configured and arranged to act with the shield layer and modified shield layer as a coaxial shield, the proximal spring assembly having a distal end, wherein the modified shield layer provides a region of stiffness transition from the shield layer to the proximal spring assembly;
a joining segment attached to the distal end of the proximal spring assembly;
a magnetic resonance imaging coil attached to the joining segment and conductively coupled to the core, the imaging coil having a distal end; and
a spring tip attached to the distal end of the imaging coil.

25. A magnetic resonance imaging probe, comprising:
a core of non-magnetic material;
a first insulator/dielectric surrounding at least a part of the core;
a shield layer surrounding at least a part of the first insulator/dielectric and having a distal end;
a modified shield layer attached to the distal end of the shield layer and having a distal end;
a joining segment attached to the distal end of the modified shield layer;
a magnetic resonance imaging coil attached to the joining segment, conductively coupled to the core, and having a distal end; and
a spring tip attached to the distal end of the imaging coil, wherein the modified shield layer provides a region of stiffness transition from the shield layer to the spring tip.

26. A magnetic resonance imaging probe system, comprising:
a magnetic resonance imaging probe, having:
a probe shaft including a distal end and a proximal end, the probe shaft further including:
a core of non-magnetic material;
a first insulator/dielectric covering the core;
a shield layer covering the first insulator/dielectric and having a distal end;
a proximal spring assembly conductively coupled to the distal end of the shield layer and having a distal end and configured and arranged to act with the shield layer as a coaxial shield; and
a magnetic resonance imaging coil non-conductively coupled to the distal end of the proximal spring assembly and conductively coupled to the core, the imaging coil having a distal end;
a spring tip;
an electrically insulating material affixing the spring tip to the distal end of the probe shaft and preventing electrical conduction between the spring tip and the imaging coil; and
a connector attached to the proximal end of the probe shaft; and
an interface, having:
a balun circuit;
a decoupling circuit in electrical communication with at least one of the balun circuit or a tuning/matching circuit;
the tuning/matching circuit in electrical communication with at least one of the balun circuit or the decoupling circuit;
a proximal connector, in electrical communication with at least one of the balun circuit, the decoupling circuit, or the tuning/matching circuit, the proximal connector being adapted for removable electrical connection to a magnetic resonance scanner; and a distal connector, in electrical communication with at least one of the balun circuit, the decoupling circuit, or the tuning/matching circuit, the connector of the interface being adapted for removable electrical connection to the connector of the imaging probe.

* * * * *